(12) United States Patent
Kanthasamy

(10) Patent No.: US 7,632,819 B1
(45) Date of Patent: Dec. 15, 2009

(54) METHODS AND COMPOSITIONS FOR INHIBITING PKC DELTA CLEAVAGE FOR TREATMENT AND PREVENTION OF NEURODEGENERATION AND APOPTOSIS

(75) Inventor: Anumantha G. Kanthasamy, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 321 days.

(21) Appl. No.: 11/262,677

(22) Filed: Oct. 31, 2005

Related U.S. Application Data

(60) Provisional application No. 60/623,527, filed on Oct. 29, 2004.

(51) Int. Cl.
*A61K 38/06* (2006.01)
*G01N 33/53* (2006.01)

(52) U.S. Cl. .................. 514/18; 530/330; 435/7.71; 930/250

(58) Field of Classification Search ........................ None
See application file for complete search history.

(56) References Cited

U.S. PATENT DOCUMENTS 6,211,334 B1 * 4/2001 Beach et al. ............. 530/350
2002/0090603 A1 * 7/2002 Lipton et al. ............. 435/4

OTHER PUBLICATIONS

Hansson, et al., 2000, Experimental Neurology, 164, 102-111.*
Kitazawa, et al., 2003, Neuroscience, 119, 945-964.*
[Retreived from]:http://www.thefreedictionary.com/ameliorating, 2008, 3 pages [Retreived on Dec. 1, 2008].*
Fuentes-Prior, Pablo et al., "The protein structures that shape caspase activity, specificity, activation and inhibition", Biochem. J. (2004), 384:201-232 (printed in Great Britain).

Wee, Lawrence JK et al., "SVM-based prediction of caspase substrate cleavage sites", BMC Bioinformatics 2006, 7(suppl 5):S14. 9 pages.
Dou, Q. Ping, "RB and Apoptotic Cell Death", Frontiers in Bioscience 3, d419-430, Apr. 16, 1998.
Kanthasamy, Anumantha G., "Role of Proteolytic Activation of Protein Kinase Cdelta in Oxidative Stress-Induced Apoptosis", Antioxidants & Redox Signaling, 5(5):609-620, 2003.
Kaul, Siddharth, "Caspase-3 dependent proteolytic activation of protein kinase Cdelta mediates and regulates 1-methyl-4-phenylpyridinium (MPP+)-induced apoptotic cell death in dopaminergic cells: relevance to oxidative stress in dopaminergic degeneration", European Journal of Neuroscience, vol. 18, pp. 1387-1401, 2003.
Kitazawa, M., "Dieldrin induces apoptosis by promoting caspase-3-dependent proteolytic cleavage of protein kinase Cdelta in dopaminergic cells: relevance to oxidative stress and dopaminergic degeneration", Neuroscience, 119, pp. 945-964, 2003
Kitazawa, Masashi, "Activation of protein kinase Cdelta by proteolytic cleavage contributes to manganese-induced apoptosis in dopaminergic cells: protective role of Bcl-2", Biochemical Pharmacology 69, pp. 133-146, 2005.
Martelli, A.M., "Nuclear protein kinase C isoforms and apoptosis", European Journal of Histochemistry, vol. 48:89-94 2004.
Spitaler, Martin, "Protein kinase C and beyond", Nature Immunology, 5(8):785-790, Aug. 2004.

* cited by examiner

*Primary Examiner*—Cecilia Tsang
*Assistant Examiner*—Satyanarayana R Gudibande
(74) *Attorney, Agent, or Firm*—McKee, Voorhees & Sease, P.L.C.

(57) ABSTRACT

Methods and compositions are provided which inhibit the apoptotic activity associated with oxidative stress in many disease states. According to the invention, inhibition of chemical cleavage of PKCδ by caspase-3 results in reduction of apoptosis. Novel peptide inhibitors with the amino acid motif Asp Ile Pro Asp (SEQ ID NO:5) are also disclosed. The peptides are useful as inhibitors of PKCδ-mediated apoptosis and oxidative stress, and other diseases regulated by a catalytically active PKCδ.

11 Claims, 17 Drawing Sheets

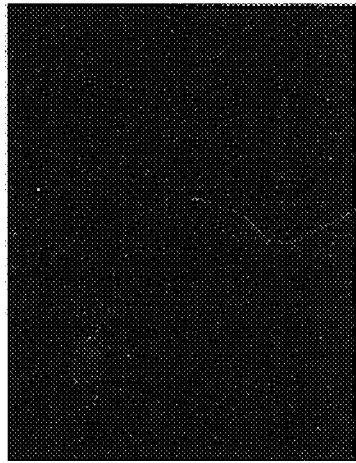
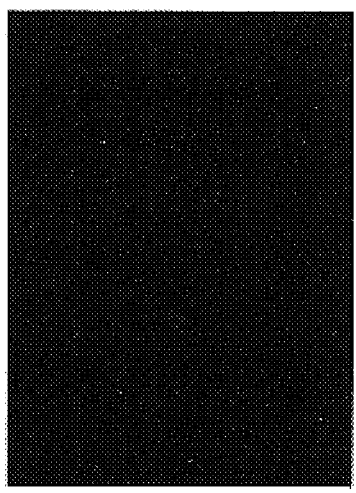
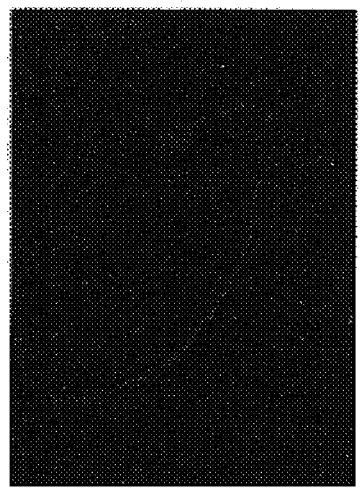
Fig. 12C

Design of triple DMQD and DMQA peptide

|  | Nucleotide sequence | Amino acid sequence |
|---|---|---|
| DMQD | 5' CACC<u>ATG</u> | <u>M</u> |
|  | GCTGGGGAG<u>GACATGCAAG</u>ACAACAGTGGG | AGE<u>DMQD</u>NSG |
|  | GCTGGGGAG<u>GACATGCAAG</u>ACAACAGTGGG | AGE<u>DMQD</u>NSG |
|  | GCTGGGGAG<u>GACATGCAAG</u>ACAACAGTGGG 3' | AGE<u>DMQD</u>NSG |
| DMQA | 5' CACC<u>ATG</u> | <u>M</u> |
|  | GCTGGGGAG<u>GACATGCAAG</u>CCAACAGTGGG | AGE<u>DMQA</u>NSG |
|  | GCTGGGGAG<u>GACATGCAAG</u>CCAACAGTGGG | AGE<u>DMQA</u>NSG |
|  | GCTGGGGAG<u>GACATGCAAG</u>CCAACAGTGGG 3' | AGE<u>DMQA</u>NSG |

*Fig.13*

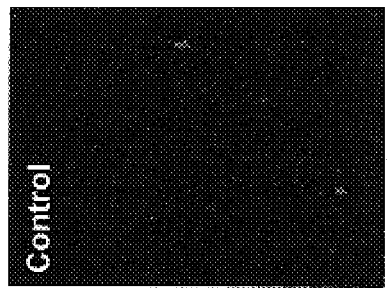
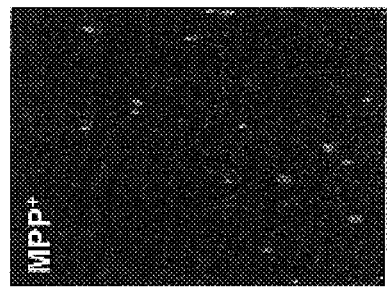
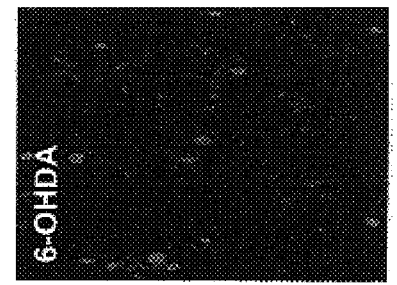
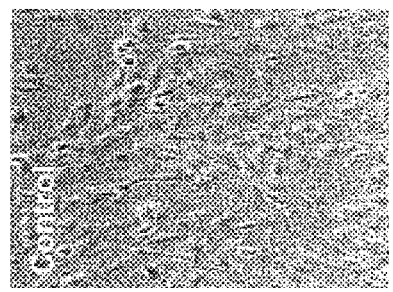
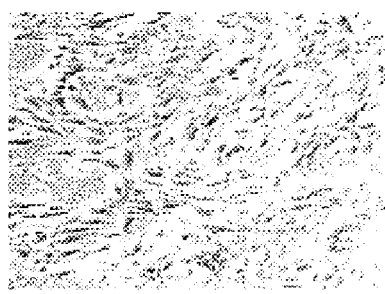
Fig. 14B

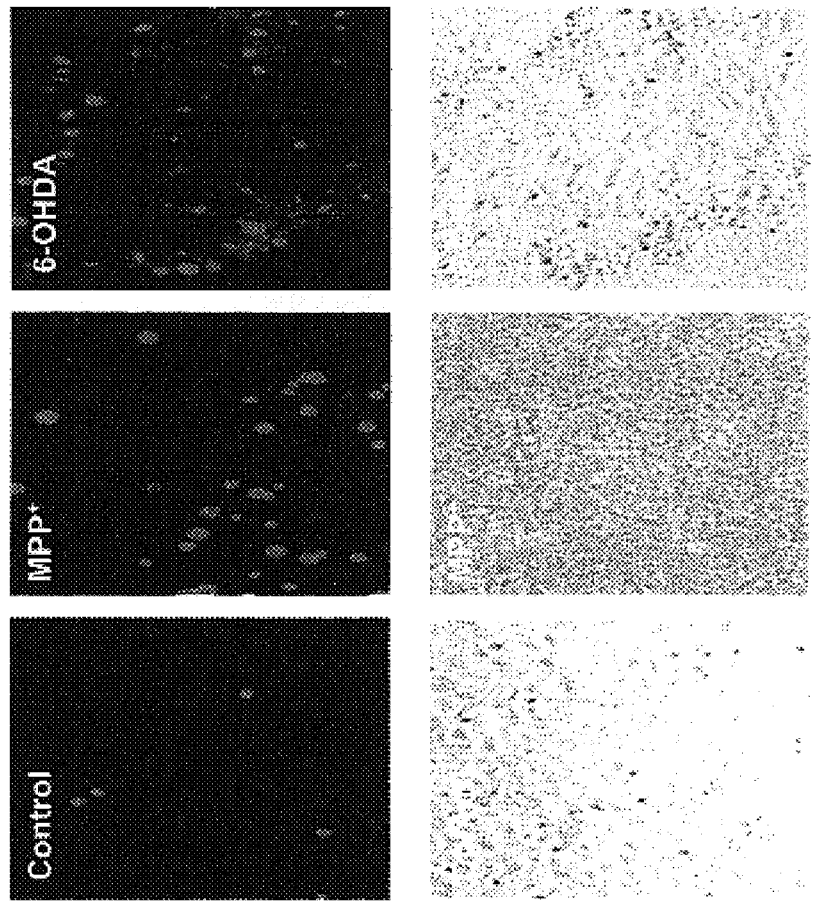

```
                        SEQUENCE LISTING

<160> NUMBER OF SEQ ID NOS: 9

<210> SEQ ID NO 1
<211> LENGTH: 30
<212> TYPE: DNA
<213> ORGANISM: artificial sequence
<220> FEATURE:
<223> OTHER INFORMATION: chemically synthesized

<400> SEQUENCE: 1
gctggggagg acatgcaaga caacagtggg                                      30

<210> SEQ ID NO 2
<211> LENGTH: 10
<212> TYPE: PRT
<213> ORGANISM: artificial sequence
<220> FEATURE:
<223> OTHER INFORMATION: chemically synthesized

<400> SEQUENCE: 2

Ala Gly Glu Asp Met Gln Asp Asn Ser Gly
1               5                   10

<210> SEQ ID NO 3
<211> LENGTH: 30
<212> TYPE: DNA
<213> ORGANISM: artificial sequence
<220> FEATURE:
<223> OTHER INFORMATION: chemically synthesized

<400> SEQUENCE: 3
gctggggagg acatgcaagc caacagtggg                                      30

<210> SEQ ID NO 4
<211> LENGTH: 10
```

```
<212> TYPE: PRT
<213> ORGANISM: artificial sequence
<220> FEATURE:
<223> OTHER INFORMATION: chemically synthesized

<400> SEQUENCE: 4

Ala Gly Glu Asp Met Gln Ala Asn Ser Gly
1               5                   10

<210> SEQ ID NO 5
<211> LENGTH: 4
<212> TYPE: PRT
<213> ORGANISM: artificial sequence
<220> FEATURE:
<223> OTHER INFORMATION: chemically synthesized

<400> SEQUENCE: 5

Asp Ile Pro Asp
1

<210> SEQ ID NO 6
<211> LENGTH: 4
<212> TYPE: PRT
<213> ORGANISM: artificial sequence
<220> FEATURE:
<223> OTHER INFORMATION: chemically synthesized

<400> SEQUENCE: 6

Asp Glu Val Asp
1

<210> SEQ ID NO 7
<211> LENGTH: 4
<212> TYPE: PRT
<213> ORGANISM: Artificial Sequence
<220> FEATURE:
<223> OTHER INFORMATION: chemically synthesized

<400> SEQUENCE: 7

Asp Met Gln Asp
1

<210> SEQ ID NO 8
<211> LENGTH: 4
<212> TYPE: PRT
<213> ORGANISM: artificial sequence
<220> FEATURE:
<223> OTHER INFORMATION: chemically synthesized

<400> SEQUENCE: 8

Asp Met Gln Ala
1

<210> SEQ ID NO 9
<211> LENGTH: 5
<212> TYPE: PRT
<213> ORGANISM: Artificial Sequence
<220> FEATURE:
<223> OTHER INFORMATION: chemically synthesized
<220> FEATURE:
<221> NAME/KEY: misc_feature
<222> LOCATION: (5)..(5)
<223> OTHER INFORMATION: X = any amino acid

<400> SEQUENCE: 9

Asp Glu Gln Asp Xaa
1               5
```

METHODS AND COMPOSITIONS FOR INHIBITING PKC DELTA CLEAVAGE FOR TREATMENT AND PREVENTION OF NEURODEGENERATION AND APOPTOSIS

CROSS-REFERENCE TO RELATED APPLICATIONS

This application claims priority under 35 U.S.C. § 119 of a provisional application Ser. No. 60/623,527 filed Oct. 29, 2004, which application is hereby incorporated by reference in its entirety.

GRANT REFERENCE

This invention was made with government support under Grant No. NS038644 awarded by the National Institutes of Health. The Government has certain rights in the invention.

FIELD OF THE INVENTION

The invention relates to the discovery of a novel target therapeutic site for many diseases associated with oxidative stress and apoptosis. More particularly, the present invention relates to inhibition of protein kinase C delta (PKCδ)-mediated apoptotic activity, including the discovery of novel peptides that inhibit cleavage of the molecule.

BACKGROUND OF THE INVENTION

Oxidative stress and apoptosis are considered common mediators of disease, including Alzheimer's disease (AD), Parkinson's disease (PD), Huntington disease (HD), Amyotrophic Lateral Sclerosis (ALS), ischemia and stroke, spinal cord trauma and head injury, cardiovascular diseases and inflammatory diseases. Despite the growing amount of information regarding the pathophysiological role of oxidative insult in the apoptotic cell death process, little effort has been made to identify the key cell signaling molecule that contributes to the cell death.

Parkinson's disease (PD) is a major common neurodegenerative disorder affecting more than 1% of the population over the age of 60 in the US (Allam et al., 2005; West et al., 2005). Selective degeneration of nigral dopaminergic neurons is the primary pathology of PD (Przedborski, 2005). Both clinical and experimental evidence clearly demonstrates that oxidative stress and apoptosis are key cellular mechanisms that contribute to the selective nigral neuronal loss (Maguire-Zeiss et al., 2005). However, the key cellular target that mediates the nigral apoptotic cell death process following oxidative insult is not completely understood.

Recently, it was reported by the inventors that proteolytic activation of PKCδ, a member of the novel PKC isoform family, plays a key role in apoptotic cell death of dopaminergic neurons in a cell culture model of PD as well as oxidative stress models (Anantharam et al., 2002; Kaul et al., 2003; Kitazawa et al., 2003; Yang et al., 2004; Latchoumycandane et al., 2005). It was demonstrated that blockade of PKCδ activation by the kinase dominant negative mutant, cleavage-resistant mutant or siRNA almost completely prevented the nigral cell death (Kaul et al., 2003; Kitazawa et al., 2003; Anantharam et al., 2004; Yang et al., 2004; Latchoumycandane et al., 2005). PKCδ is proteolytically cleaved by caspase-3 at the 324DIPD327 (SEQ ID NO:5) residue, resulting in 41-kDa catalytic and 38-kDa regulatory subunits, leading to a persistent activation of the kinase (Kaul et al., 2003; Anantharam et al., 2004; Yang et al., 2004).

Protein kinase C (PKC) belongs to a family of serine threonine protein kinases. To date, twelve isoforms in the PKC subfamily have been identified. Kanthasamy et al., 2003; Antioxidants & Redox Signaling, 5: 609-620. One such isoform is protein kinase C delta (PKCδ). Martelli A M, Mazzotti G, Capitani S, Nuclear protein kinase C isoforms and apoptosis. Eur J Histochem. 2004; 48(1):89-94.

PKCδ was originally discovered by Gschwendt et al. in 1986, Gschwendt M, Kittstein W, and Marks F. A novel type of phorbol ester-dependent protein phosphorylation in the particulate fraction of mouse epidermis. Biochem Biophys Res Commun. 137: 766-74, 1986, and cloned from a rat brain cDNA library the following year. Kurkinen K M, Keinanen R A, Karhu R, and Koistinaho J. Genomic structure and chromosomal localization of the rat protein kinase Cdelta-gene. Gene 242: 115-23, 2000, Ono Y, Fujii T, Ogita K, Kikkawa U, Igarashi K, and Nishizuka Y. Identification of three additional members of rat protein kinase C family: delta-, epsilon- and zeta-subspecies. FEBS Lett. 226: 125-8, 1987. The PKCδ gene is localized on human chromosome 3, Huppi K, Siwarski D, Goodnight J, and Mischak H. Assignment of the protein kinase C delta polypeptide gene (PRKCD) to human chromosome 3 and mouse chromosome 14. Genomics 19: 161-2, 1994, rat chromosome 16, Kurkinen K M, Keinanen R A, Karhu R, and Koistinaho J. Genomic structure and chromosomal localization of the rat protein kinase Cdelta-gene. Gene 242: 115-23, 2000, and mouse chromosome 14, Huppi K, Siwarski D, Goodnight J, and Mischak H. Assignment of the protein kinase C delta polypeptide gene (PRKCD) to human chromosome 3 and mouse chromosome 14. Genomics. 19: 161-2, 1994.

There exists a substantial body of evidence that indicates that PKCδ plays a fundamental role in apoptosis. PKCδ has been shown to accumulate in the nucleus of C5 cells, in response to etoposide treatment. Martelli A M, Mazzotti G, Capitani S, Nuclear protein kinase C isoforms and apoptosis. Eur J Histochem. 2004; 48(1):89-94. Overexpression of PKCδ-catalytic fragment results in nuclear localization of the PKCδ fragment and apoptosis. Martelli A M, Mazzotti G, Capitani S, Nuclear protein kinase C isoforms and apoptosis. Eur J Histochem. 2004; 48(1):89-94. It is believed that active PKCδ binds to the carboxyl-terminus of DNA-dependent protein kinase (DNA-PK), an enzyme involved in the repair of DNA strand breaks. Once bound, the active PKCδ binds to and phosphorylates the DNA-PK. Consequently, the DNA-PK dissociates from the DNA, impedes the repair of DNA strand breaks, and results in DNA fragmentation, one of the hallmarks of apoptosis.

Apoptosis, a genetically programmed form of cell death, is required for normal development, tissue homeostasis and the elimination of damaged cells. However, an increase or decrease in apoptosis may contribute to the pathology of a wide range of disorders and diseases. It has been proposed that apoptosis plays a central role in several human neurodegenerative diseases, including Alzheimer's disease (AD), Parkinson's disease (PD), Huntington disease (HD), amyotrophic lateral sclerosis (ALS), ischemia and stroke, cardiovascular diseases, inflammatory diseases, spinal cord trauma, and head injury.

It is an object of the present invention to provide novel compositions and methods which inhibit the caspase mediated cleavage of PKCδ.

It is another object of the invention to provide a novel target site for therapeutic intervention to prevent neurodegenerative apoptosis.

It is yet another object of the invention to provide pharmaceutical composition for the treatment, or amelioration of symptoms or protection from further damage in Alzheimer's disease (AD), Parkinson's disease (PD), Huntington disease (HD), Amyotrophic Lateral Sclerosis (ALS), ischemia and stroke, spinal cord trauma and head injury, cardiovascular diseases, inflammatory diseases, and other disease states associated with oxidative stress and apoptosis.

It is yet another object of the invention to prevent oxidative stress and apoptosis in an animal.

SUMMARY OF THE INVENTION

The present invention includes several compositions and methods to make and use protein kinase C delta (PKCδ) peptide cleavage inhibitors involved in inhibiting PKCδ-mediated apoptotic activity.

In one aspect of the present invention, a PKCδ peptide cleavage inhibitor is provided in which the inhibitor includes the following amino acid motif Asp Ile Pro Asp (SEQ ID NO:5), (Aspartic Acid, Isoleucine, Proline, and Aspartic Acid).

The present invention is also directed to a nucleic acid that encodes a peptide or polypeptide containing the amino acid motif Asp Ile Pro Asp (SEQ ID NO:5) where the translated polypeptide inhibits PKCδ-mediated apoptotic activity.

In another aspect of the invention, the PKCδ peptide cleavage inhibitor may be cleaved by caspase-3.

The PKCδ peptide cleavage inhibitors are useful for treating diseases and disorders characterized by apoptosis and oxidative stress, for example, as Alzheimer's disease (AD), Parkinson's disease (PD), Huntington disease (HD), and amyotrophic lateral sclerosis (ALS), ischemia and stroke, cardiovascular diseases, inflammatory diseases, spinal cord trauma, and head injury. Therefore, in addition to use as therapeutics the PKCδ peptide cleavage inhibitors are useful as tools in the areas of apoptotic research and for the diagnosis of diseases or disorders characterized by apoptosis or oxidative stress. Thus the invention also includes methods of treating these diseases by inhibiting PKCδ cleavage by use of the peptide inhibitors disclosed herein or by other methods disclosed herein. The invention provides PKCδ as a novel target site for therapeutic intervention in treatment of such diseases in the development of further additional therapeutics etc.

In yet another aspect of the present invention, a pharmaceutical composition comprising a PKCδ peptide cleavage inhibitor and a pharmaceutically acceptable carrier is provided. This composition may be used in the treatment of a biological condition mediated by PKCδ, including those characterized by apoptosis or oxidative stress.

In still another aspect of the present invention, a method of inhibiting PKCδ activity, is provided where a PKCδ peptide cleavage inhibitor is administered to a cell, the inhibitor cleaved by caspase-3, thereby inhibiting PKCδ apoptotic activity.

In yet another aspect of the present invention, a method of selecting a PKCδ peptide cleavage inhibitor for the ability to inhibit PKCδ-mediated apoptotic activity is provided to a cell containing a PKCδ protein or polypeptide upon which caspase-3 acts enzymatically, a PKCδ peptide cleavage inhibitor, and an agent that induces apoptosis is administered to a cell containing caspase-3. The presence or absence of genomic DNA fragmentation produced as a result of the enzymatic reaction between PKCδ and caspase-3 may be determined using a genomic DNA fragmentation assay. The absence of DNA fragmentation indicates that PKCδ-mediated apoptosis has been inhibited by the PKCδ peptide cleavage inhibitor, whereas the presence of DNA fragmentation indicates that PKCδ-mediated apoptosis has not been inhibited by the PKCδ peptide cleavage inhibitor.

The PKCδ peptide cleavage inhibitors are useful as inhibitors of apoptosis and oxidative stress and can be employed as therapeutic agents for diseases characterized by apoptosis and oxidative stress, including Alzheimer's disease (AD), Parkinson's disease (PD), Huntington disease (HD), amyotrophic lateral sclerosis (ALS), ischemia and stroke, cardiovascular diseases, inflammatory diseases, spinal cord trauma, and head injury.

The Inventor contemplates that the PKCδ peptide cleavage inhibitors may be useful as inhibitors for other substrates of caspase-3. These include but are not limited to poly(ADP-ribose) polymerase (PARP), U1 snRNP (U1-70 kDa), the 450-kDa catalytic subunit of DNA dependent protein kinase (DNA-PK(cs)), Huntingtin, Sterol Regulatory Element Binding Proteins-1 and -2 (SREBP-1 and SREBP-2), retinoblastoma tumor suppressor gene (Rb), and DNA Fragment Factor (DFF). Furthermore, it is contemplated that the PKCδ peptide cleavage inhibitors may be useful as inhibitors for other caspases and their cognate substrates.

The PKCδ peptide cleavage inhibitors can be utilized in apoptotic research and in diagnosis and/or treatment of diseases and disorders characterized by apoptosis and oxidative stress.

BRIEF DESCRIPTION OF THE DRAWINGS

FIGS. 12A-12D show that z-DIPD-fmk (SEQ ID NO:5) protects against MPP$^+$- and 6-OHDA-induced TH neuronal cell and neurite loss. Quantitative data of TH cell count and neuronal process length in image sets A and B are shown in B, MPP$^+$ and D, 6-OHDA respectively.

FIG. 13 shows the design of triple tandem human PKCδ cleavage site motif DMQD (SEQ ID NO:7) and cleavage site resistant motif DMQA (SEQ ID NO:8). The oligonucleotide and amino acid sequence for the human PKCδ cleavage site motif DMQD (SEQ ID NO:7) are set forth in SEQ ID NOS: 1 and 2 respectively. The oligonucleotide and amino acid sequence for the human PKCδ cleavage resistant motif DMQA (SEQ ID NO:8) are set forth in SEQ ID NOS:3 and 4 respectively.

FIGS. 14A-14C show that the expression of DMQD (SEQ ID NO:7) and DMQA (SEQ ID NO:8) protects against MPP$^+$- and 6-OHDA-induced cytotoxicity in N27 mesencephalic neuronal cells. A) Control N27 cells treated with MPP$^+$ and 6-OHDA. B) DMQD (SEQ ID NO:7)-transfected cells treated with MPP$^+$ and 6-OHDA, and C) DMQA (SEQ ID NO:8) transfected cells treated with MPP$^+$ and 6-OHDA. Increase in number of Sytox green fluorescence cells represents increase in neurotoxicity. DMQD (SEQ ID NO:7) and DMQA (SEQ ID NO:8) transfected cells protected against MPP$^+$ and 6-OHDA neurotoxicity as demonstrated by the lower number of Sytox green fluorescence positive cells as compared to control cells.

DETAILED DESCRIPTION OF INVENTION

Figure 1:
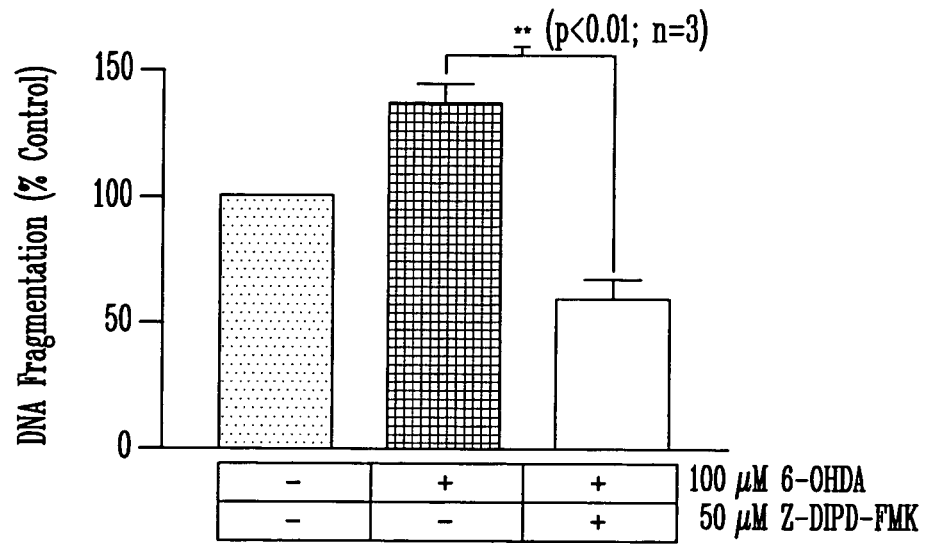
FIG. 1—Antiapoptotic effect of Asp Ile Pro Asp (SEQ ID NO:5) in 6-OHDA model.

The present invention is based on the discovery that peptides containing the amino acid motif Asp Ile Pro Asp (SEQ ID NO:5) inhibit PKCδ-mediated apoptosis in vitro. It is believed that the mechanism for inhibiting PKCδ-mediated apoptotic activity results from a peptide containing the amino acid motif Asp Ile Pro Asp (SEQ ID NO:5) competing with PKCδ as a substrate of caspase-3, thereby preventing caspase-3 from catalytically activating PKCδ. PKCδ is proteolytically cleaved by caspase-3 into a 41 kDa catalytic subunit and a 38 kDa regulatory subunit, leading to a persistent activation of the kinase during oxidative insults and apoptosis. Kaul S, Kanthasamy A, Kitazawa M, Anantharam V, Kanthasamy A G, Caspase-3 dependent proteolytic activation of protein kinase C delta mediates and regulates 1-methyl-4-phenylpyridinium (MPP$^+$)-induced apoptotic cell death in dopaminergic cells: relevance to oxidative stress in dopaminergic degeneration. Eur J. Neurosci. 2003 September; 18(6):1387-401).

In another embodiment of the present invention, the PKCδ peptide cleavage inhibitor is chemically modified to protect the inhibitor from protease degradation. Methods to prevent the protease degradation are known to one skilled in the art, including the addition of N-benzyloxycarbonyl at the N-terminal of the polypeptide. Peptides can be synthesized by methods known to one skilled in the art or isolated from cells or tissues of organisms using standard methods known in the art.

In yet another embodiment, the PKCδ peptide cleavage inhibitor is chemically modified to contain a (O-methyl)fluoromethyl ketone (FMK) tail. Tails may facilitate the inhibitor in permeating cell membranes. Other tails that facilitate cell membrane permeability are well known in the art. These include, but are not limited to, N-Acetyl or chloromethyl ketone derivatives.

The invention also contemplates nucleic acid sequences that encode PKCδ peptide cleavage inhibitors. These sequences can be determined using genetic codon degeneracy and synthesized or isolated according to techniques known in the art. It will also be recognized by one skilled in the art that nucleic acid sequences encoding PKCδ peptide cleavage inhibitors may be cloned into a vector and expressed in cells. The inhibitor may then be isolated using standard techniques, for example fusion tags, known to one skilled in the art. Therefore, another embodiment of the present invention is a nucleic acid that upon transcription, translation, and chemical modification produces a peptide that is able to inhibit PKCδ-mediated apoptotic activity.

When the PKCδ peptide cleavage inhibitors of the present invention are added to living mammalian cells, these inhibitors are believed to be cleaved by caspase-3, thereby inhibiting caspase-3 from binding and cleaving PKCδ. PKCδ can be delivered intracellularly using a lipid-mediated protein delivery system. Kaul S, Kanthasamy A, Kitazawa M, Anantharam V, Kanthasamy A G, Caspase-3 dependent proteolytic activation of protein kinase C delta mediates and regulates 1-methyl-4-phenylpyridinium (MPP$^+$)-induced apoptotic cell death in dopaminergic cells: relevance to oxidative stress in dopaminergic degeneration. Eur J. Neurosci. 2003 September; 18(6): 1387-401. The incomplete cleavage of PKCδ or PKCδ-mediated apoptotic inhibition can be measured using standard techniques known to one skilled in the art. Yoshimura S, Banno Y, Nakashima S, Takenaka K, Sakai H, Nishimura Y, Sakai N, Shimizu S, Eguchi Y, Tsujimoto Y, Nozawa Y. Ceramide formation leads to caspase-3 activation during hypoxic PC12 cell death. Inhibitory effects of Bcl-2 on ceramide formation and caspase-3 activation. J Biol. Chem. 1998 Mar. 20; 273(12):6921-7 (describing a method to determine caspase activity). Kaul S, Kanthasamy A, Kitazawa M, Anantharam V, Kanthasamy A G, Caspase-3 dependent proteolytic activation of protein kinase C delta mediates and regulates 1-methyl-4-phenylpyridinium (MPP$^+$)-induced apoptotic cell death in dopaminergic cells: relevance to oxidative stress in dopaminergic degeneration. Eur J. Neurosci. 2003 September; 18(6):1387-401) (describing the use of PKCδ-specific antibodies). Reyland M E, Anderson S M, Matassa A A, Barzen K A, Quissell D O. Protein kinase C delta is essential for etoposide-induced apoptosis in salivary gland acinar cells. J Biol. Chem. 1999 Jul. 2; 274(27):19115-23), Anantharam V, Kitazawa M, Wagner J, Kaul S, Kanthasamy A G. Caspase-3-dependent proteolytic cleavage of protein kinase Cdelta is essential for oxidative stress-mediated dopaminergic cell death after exposure to methylcyclopentadienyl manganese tricarbonyl. J. Neurosci. 2002 Mar. 1; 22(5):1738-51, (describing assaying for PKCδ enzymatic activity using an immunoprecipitation assay).

In the present invention, the PKCδ peptide cleavage inhibitor inhibits PKCδ-mediated apoptotic activity in cell culture models of Parkinson's disease where apoptosis is induced by MPP+ or 6-OHDA. MPP+ not only promotes apoptosis but has also been shown to promote caspase activation. Kaul S, Kanthasamy A, Kitazawa M, Anantharam V, Kanthasamy A G, Caspase-3 dependent proteolytic activation of protein kinase C delta mediates and regulates 1-methyl-4-phenylpyridinium (MPP+)-induced apoptotic cell death in dopaminergic cells: relevance to oxidative stress in dopaminergic degeneration. Eur J. Neurosci. 2003 September; 18(6):1387-401).

Figure 2:
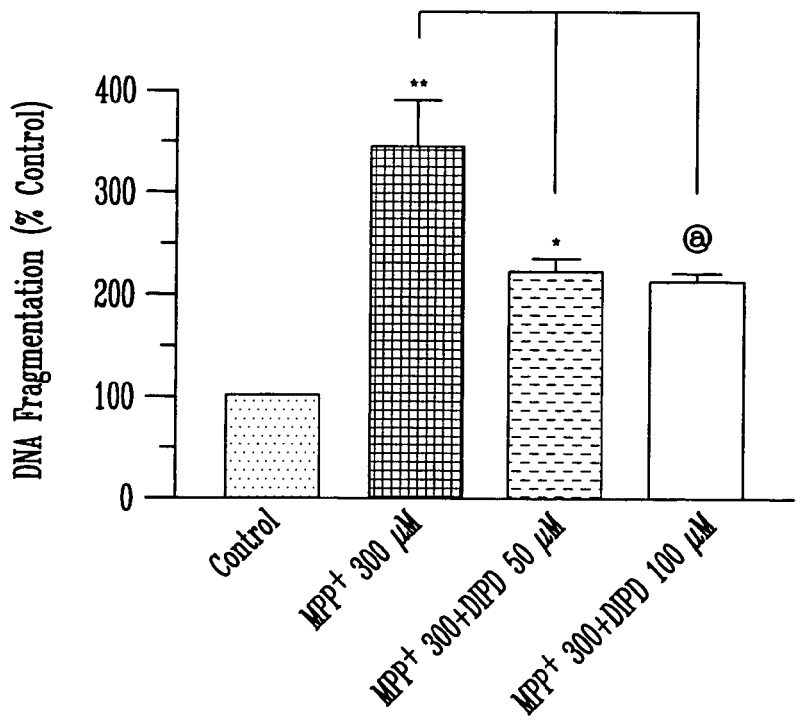
FIG. 2—Antiapoptotic effect of Asp Ile Pro Asp (SEQ ID NO:5) in MPP$^+$ Model of PD.
Figure 3:
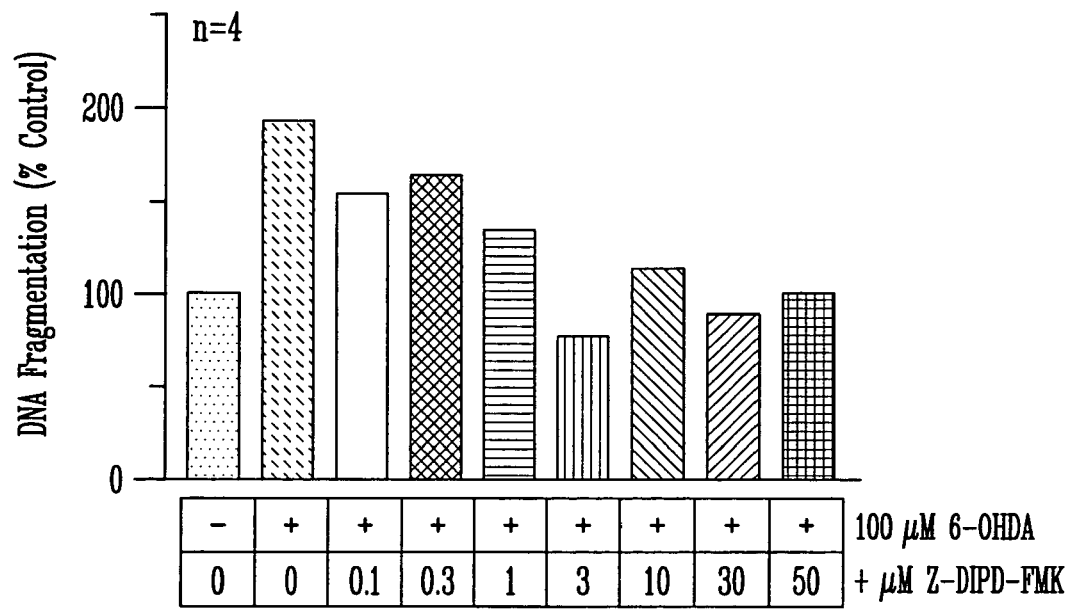
FIG. 3—Dose-response effect of Asp Ile Pro Asp (SEQ ID NO:5) in 6-OHDA Model of PD.

In one embodiment of the present invention, the peptide cleavage inhibitor N-benzyloxycarbonyl-Asp(OMe)-Ile-Pro-Asp(OMe)-FMK (SEQ ID NO:5) effectively blocked 6-OHDA-induced DNA fragmentation as shown in FIG. 1. Furthermore, the inhibitor also inhibited 1-MPP+ induced DNA fragmentation as shown in FIG. 2. These results, as measured using genomic DNA fragmentation assays, indicate that these PKCδ peptide cleavage inhibitors protect dopaminergic neuronal cells against apoptosis and have neuroprotective effects Furthermore, the Inventors have found that using a concentration of N-benzyloxycarbonyl-Asp(OMe)-Ile-Pro-Asp(OMe)-FMK (SEQ ID NO:5) as low as 3 μM almost completely inhibits 6-OHDA-induced DNA fragmentation as shown in FIG. 3. benzyloxycarbonyl-Asp(OMe)-Ile-Pro-Asp(OMe)-FMK (SEQ ID NO:5) as low as 3 μM almost completely inhibits 6-OHDA-induced DNA fragmentation as shown in FIG. 3.

Figure 4:
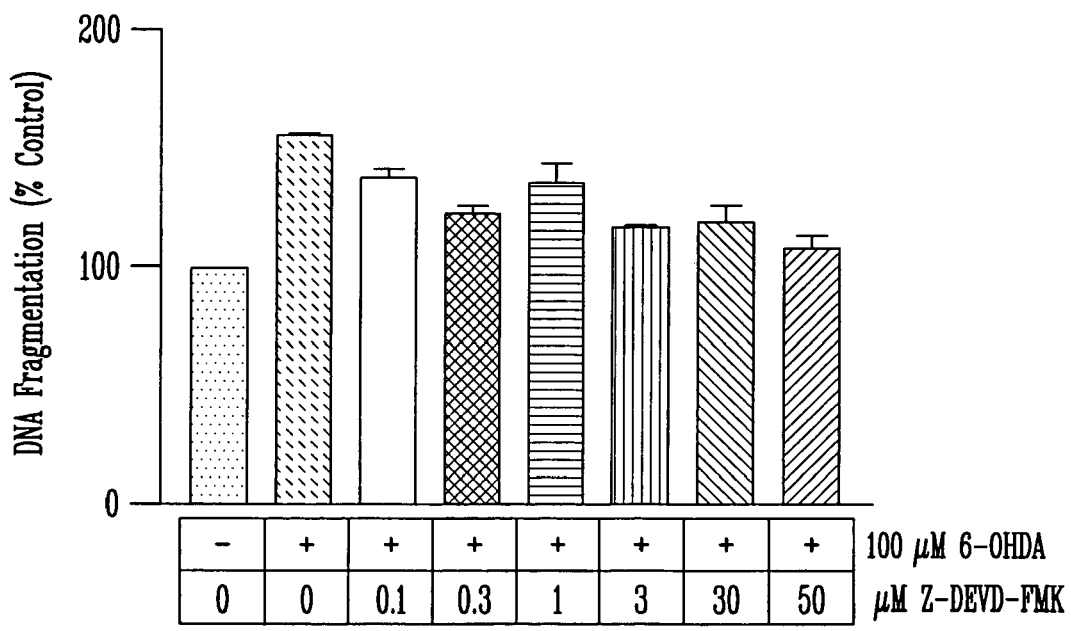
FIG. 4—Antiapoptotic effect of Asp Ile Pro Asp (SEQ ID NO:5) as compared to DEVD-FMK (SEQ ID NO:6) in 6-OHDA model.

Remarkably, the Inventors have found that N-benzyloxycarbonyl-Asp(OMe)-Ile-Pro-Asp(OMe)-FMK (SEQ ID NO:5) is more potent than other known peptides in attenuating apoptosis as shown in FIG. 4. The Inventors have found the N-benzyloxycarbonyl-Asp(OMe)-Ile-Pro-Asp(OMe)-FMK (SEQ ID NO 5) PKCδ,peptide cleavage inhibitor is more potent than the classical caspase-3 inhibitor Asp-Glu-Val-Asp-FMK (SEQ ID NO:6) in attenuating apoptosis (FIG. 4).

Accordingly, the invention relates to the active site of PKCδ cleavage by caspase as a novel target for treatment and amelioration of symptoms of diseases and/or disorders characterized by apoptosis, according to the invention any method of altering or otherwise preventing cleavage of this site may be used as a treatment of such diseases. This may include such things as site directed mutagenesis, compounds which sterically hinder the binding of caspase, compounds which actively and irreversibly bind caspase, as well as the novel peptide compounds of the invention. Such inhibitors can be employed as a therapeutic agent for diseases or disorders characterized by apoptosis. For example, in another embodiment of the present invention, a pharmaceutical composition comprised of a PKCδ peptide cleavage inhibitor containing the amino acid motif Asp Ile Pro Asp (SEQ ID NO:5) and a pharmaceutically acceptable carrier is capable of inhibiting PKCδ-mediated apoptotic activity. Therefore, the pharmaceutical composition may be used in the treatment of a disease or disorder mediated by ischemia and stroke, cardiovascular diseases, inflammatory diseases, spinal cord trauma, and head injury.

The present invention contemplates methods of inhibiting PKCδ-mediated apoptotic activity using a PKCδ peptide cleavage inhibitor, N-benzyloxycarbonyl-Asp Ile Pro Asp (SEQ ID NO:5), where the PKCδ peptide cleavage inhibitor inhibits PKCδ-mediated apoptotic activity in the presence of an apoptotic inducing agent. Agents that induce apoptosis are known to one skilled in the art, including chemicals, physical insults, viruses, cytokines, and withdrawal of trophic factors. Chemicals that induce apoptosis include neurotoxins, chemotherapeutic agents, glucocorticoids, free-radicals, glutamate, calcium, azide, and hydrogen peroxide. Current studies of work have shown that environmental factors, for example, pesticides, herbicides, heavy metals and elements, such as manganese, also induce apoptosis. Kitazawa M, Anantharam V, Kanthasamy A G, Dieldrin induces apoptosis by promoting caspase-3-dependent proteolytic cleavage of protein kinase Cdelta in dopaminergic cells: relevance to oxidative stress and dopaminergic degeneration. Neuroscience. 2003; 119(4):945-64. (showing that the pesticide dieldrin induces apoptosis by promoting capase-3 dependent proteolytic cleavage of PKCδ in dopaminergic cells). Kitazawa M, Anantharam V, Yang Y, Hirata Y, Kanthasamy A, and Kanthasamy A G. Activation of protein kinase Cδ by proteolytic cleavage contributes to manganese-induced apoptosis in dopaminergic cells: protective role of Bcl-2. Biochemical Pharmacology, Oct. 22, (2004). Both 1-methyl-4-phenylpyridinium (MPP+)+ and 6-hydroxydopamine (6-OHDA) are neurotoxins used in cellular models of Parkinson's disease because they are able to induce apoptosis.

hydroxydopamine (6-OHDA) are neurotoxins used in cellular models of Parkinson's disease because they are able to induce apoptosis.

In the present invention, methods of screening and selecting potential therapeutic compounds for their ability to act as a PKCδ peptide cleavage inhibitor and thus inhibit apoptotic activity are contemplated. In one embodiment, the potential PKCδ peptide cleavage inhibitor is administered to living cells. If the cell does not contain a protein or polypeptide with a PCKδ cleavage site upon which caspase-3 acts enzymatically or caspase-3, then vectors expressing these proteins can be transfected using standard techniques known to one skilled in the art. Therefore, the PKCδ substrate and/or caspase-3 may be endogeneous or exogenous in origin. Kaul S, Kanthasamy A, Kitazawa M, Anantharam V, Kanthasamy A G, Caspase-3 dependent proteolytic activation of protein kinase C delta mediates and regulates 1-methyl-4-phenylpyridinium (MPP+)-induced apoptotic cell death in dopaminergic cells: relevance to oxidative stress in dopaminergic degeneration. Eur J. Neurosci. 2003 September; 18(6):1387-401. (noting that PKCδ can be delivered intracellularly using a lipid-mediated protein delivery system.).

The cleavage of PKCδ into two subunits of 41 kDa and a 38 kDa by caspase-3 may be determined using Western blot analysis or enzymatic assays. For example, PKCδ enzymatic activity can be assayed using an immunoprecipitation assay as previously described. Reyland M E, Anderson S M, Matassa A A, Barzen K A, Quissell D O. Protein kinase C delta is essential for etoposide-induced apoptosis in salivary gland acinar cells. J Biol. Chem. 1999 Jul. 2; 274(27):19115-23, Anantharam V, Kitazawa M, Wagner J, Kaul S, Kanthasamy A G. Caspase-3-dependent proteolytic cleavage of protein kinase Cdelta is essential for oxidative stress-mediated dopaminergic cell death after exposure to methylcyclopentadienyl manganese tricarbonyl. J Neurosci. 2002 Mar. 1; 22(5):1738-51. Kaul S, Kanthasamy A, Kitazawa M, Anantharam V, Kanthasamy A G, Caspase-3 dependent proteolytic activation of protein kinase C delta mediates and regulates 1-methyl-4-phenylpyridinium (MPP$^+$)-induced apoptotic cell death in dopaminergic cells: relevance to oxidative stress in dopaminergic degeneration. Eur J. Neurosci. 2003 September; 18(6):1387-401) (describing antibodies specific for PKCδ).

In another embodiment, apoptotic activity can be assayed using standard techniques known to one skilled in the art, including commercially available assays. These include apoptotic DNA Ladder assays, Cell Death Detection ELISA$^{PLUS}$ (from Roche Applied Sciences), Caspase-3 Activity Assay-$^{PLUS}$ (from Roche Applied Sciences), terminal deoxynucleotidyl transferase-mediated dUTP [deoxy-uridine triphosphate] nick end labeling (TUNEL) assays. DNA-binding dyes or stains such as Hoechst 3342 or DAPI or propidium iodide may be used to assess nuclear morphology and DNA damage. Kaul S, Kanthasamy A, Kitazawa M, Anantharam V, Kanthasamy A G, Caspase-3 dependent proteolytic activation of protein kinase C delta mediates and regulates 1-methyl-4-phenylpyridinium (MPP$^+$)-induced apoptotic cell death in dopaminergic cells: relevance to oxidative stress in dopaminergic degeneration. Eur J. Neurosci. 2003 September; 18(6):1387-401. For example, when using genomic DNA fragmentation assays, the presence of genomic DNA fragmentation indicates that the candidate PKCδ peptide cleavage inhibitor has not inhibited PKCδ-mediated apoptotic activity and that the inhibitor failed to inhibit an enzymatic reaction between the PKCδ substrate and the caspase-3. In contrast, the absence of DNA fragmentation indicates that PKCδ-mediated activity has been inhibited by the candidate PKCδ peptide cleavage inhibitor. Therefore, the present invention allows for uses in apoptotic research, diagnosis, and therapeutics.

All publications and patents mentioned in the above specification are herein incorporated by reference. Various modifications and variations of the described method and system of the invention will be apparent to those skilled in the art without departing from the scope and spirit of the invention. Therefore, the following Examples are offered for the purpose of illustrating the present invention and are not to be construed to limit the scope of this invention.

EXAMPLES

Example 1

Design and Synthesis of Z-Asp(OMe)-Ile-Pro-Asp(OMe)-FMK (SEQ ID NO:5) peptide

The sequence of rat PKCδ cleavage site Asp Ile Pro Asp (SEQ ID NO:5) was determined by blast analysis using Vector NTI software. The amino acids were chemically modified to prevent the degradation by cellular proteases. Chemically modified tetra peptide Z-Asp(OMe)-Ile-Pro-Asp(OMe) (SEQ ID NO:5)—with fluoromethyl ketone (FMK) tail was custom synthesized at Enzyme Systems.

Example 2

Cell Culture

Undifferentiated rat mesencephalic dopaminergic (N27) cells were grown in RPMI 1640 medium containing 10% fetal bovine serum, 2 mM L-glutamine, 50 units penicillin and 50 μg/ml streptomycin. Cells were grown in a humidified atmosphere of 5% $CO_2$ at 37° C. as previously described, and 4-5 day-old cells were used for the experiments.

Example 3

Treatment Paradigm

N27 cells were pretreated with different concentrations Z-Asp(OMe)-Ile-Pro-Asp(OMe) (SEQ ID NO:5)-FMK for 45 min and then treated with 300/aM MPP$^+$ or 100 μM 6-OHDA for 24 hrs. Z is the abbreviation for N-benzyloxycarbonyl. Untreated cells were used as control samples. After the treatment, the cells were collected by trypsinization (Trypsin 0.25%, 1 mM EDTA), centrifuged at 200×g for 5 min, washed with PBS twice, then lysed. The lysate was used for DNA fragmentation assay.

Example 4

DNA Fragmentation Assay

DNA fragmentation assays were performed using a recently developed Cell Death Detection ELISA Plus Assay Kit. This is a fast, highly sensitive and reliable assay for the detection of early changes in apoptotic cell death. After treatments, 20 μl of cell lysate was processed according to the manufacturer's protocol. The assay solution consisted of a mixture of anti-histone biotin and anti-DNA-HRP directed against various histones and antibodies to both single stranded DNA and double stranded DNA, the major constituents of nucleosomes. After 2 hr incubation, unbound components were removed by washing with the incubation buffer supplied with the kit. Quantification of the nucleosomes retained by anti-DNA-HRP in the immunocomplex was determined spectrophotometrically with ABTS (2,2'-azino-di[3-ethoxybenzyl thiazoline sulfonate) as a HRP substrate (supplied with the kit). Measurements were made at 405 nm against an ABTS solution as a blank (reference wave length 490 nm).

Example 5

A Novel PKC Delta (PKCδ) Inhibitor Protects Against Oxidative Stress-Induced Apoptotic Cell Death in Neurodegenerative Disease Models Oxidative stress and apoptosis are considered common mediators of many diseases including Alzheimer's and Parkinson's diseases (PD). Recently, we identified that PKCδ, a member of the novel PKC isoform family, is proteolytically cleaved by caspase-3 into 41 kDa catalytic and 38 kDa regulatory subunits, leading to a persistent activation of the kinase during oxidative insults (Kaul et al., 2003; Yang et al., 2004). Upon further characterization using a dominant negative mutant or siRNA, we found that the proteolytic activation of PKCδ mediates apoptosis in neuronal cell culture models. Since caspase-3 cleaves PKCδ at the 324DIPD327 (SEQ ID NO:5)-site to activate the kinase, we developed an irreversible and competitive peptide inhibitor, ZAsp(OMe)-Ile-Pro-Asp(OMe)-FMK (z-DIPD-fmk) (SEQ ID NO:5), for the cleavage site and tested its efficacy against oxidative stress-induced cell death in PD models. Co-treatment of z-DIPD-fmk (SEQ ID NO:5) with the Parkinsonian toxins MPP$^+$ and 6-OHDA dose-dependently attenuated cytotoxicity, caspase-3 activation and DNA fragmentation in a mesencephalic dopaminergic neuronal cell model (N27 cells). The PKCδ peptide z-DIPD-fmk (SEQ ID NO:5) was much more potent ($IC_{50}$ 6 μM) than the caspase-3 inhibitor z-DEVD-fmk (SEQ ID NO:6) ($IC_{50}$ 18 μM). Additionally, z-DIPD-fmk (SEQ ID NO:5) effectively blocked PKCδ cleavage and proteolytic activation in PD models. Importantly, the PKCδ cleavage inhibitor z-DIPD-fmk (SEQ ID NO:5) completely rescued tyrosine hydroxylase positive neurons from $MPP^+$- and 6-OHDA-induced toxicity in mouse primary mesencephalic cultures. Furthermore, we designed lentiviral constructs that express the triple tandem human PKCδ cleavage (DMQD) (SEQ ID NO:7) and cleavage-resistant (DMQA) (SEQ ID NO:8) motifs. These constructs were significantly neuroprotective in cell culture models of PD. Collectively, these results demonstrate that the PKCδ cleavage site is a novel target for development of neuroprotective therapeutic strategies for various neurodegenerative disorders in which oxidative stress is a major mechanism of neurodegeneration. z-DIPD-fmk (SEQ ID NO:5) effectively protects against oxidative-induced neuronal apoptosis in neurodegenerative models.

Materials and Methods

Chemicals. Protease cocktail, ATP, protein-A-sepharose, protein-G-sepharose and anti-â-actin antibody were obtained from Sigma-Aldrich (St. Louis, Mo.); mouse tyrosine hydroxylase antibody was purchased from Chemicon (Temecula, Calif.); the rabbit polyclonal antibody for tyrosine hydroxylase was obtained from Calbiochem Bioscience, Inc. (King of Prussia, Pa.); rabbit PKCδ antibody was purchased from Santa Cruz Biotechnology, Inc. (Santa Cruz, Calif.); anti-rabbit and anti-mouse secondary antibodies and the ECL chemiluminescence kit were purchased from Amersham Pharmacia Biotech. (Piscataway, N.J.). Alexa 488 conjugated antirabbit/mouse, Cy3 conjugated anti-rabbit/mouse antibody and Hoechst 33342 were purchased from Molecular Probes, Inc. (Eugene, Oreg.). [ã-$_{32}$P]ATP was purchased from Perkin Elmer Life Science Products (Boston, Mass.). The Bradford protein assay kit was purchased from Bio-Rad Laboratories (Hercules, Calif.). RPMI, fetal bovine serum, -glutamine, penicillin, and streptomycin were purchased from Invitrogen (Gaithersburg, Md.). Quantity One 4.2.0 software was purchased from Bio-Rad.

Design and synthesis of z-DIPD-fmk (SEQ ID NO:5). To develop a cell permeable peptide inhibitor to specifically block PKCδ cleavage, we designed the tetrapeptide Asp-Ile-Pro-Asp (DIPD) (SEQ ID NO:5) corresponding to position 324-327 in rat PKCδ cDNA representing the caspase-3 cleavage site. Since this peptide is directed against the caspase-3 cleavage site of PKCδ, it should prevent the proteolytic cleavage and activation of PKCδ mediated by caspase-3. The custom synthesis of the tetrapeptide Z-Asp(OMe)-Ile-Pro-Asp (OMe)-FMK (SEQ ID NO:5) was performed at MP Biomedicals (Irvine, Calif.), a quality company that specializes in developing cell permeable peptide inhibitors directed against apoptosis cell signaling molecules. Briefly, the synthesis was performed with the reaction of Boc-D(OMe)-OH with MBFM (Magnesium benzyl fluoromalonate) to produce Beta-Keto fluoroester, followed by hydrogenation with Pd/c to produce Boc-D(OMe)FK, which was converted into Tfa salt using trifluoroacetic acid. Coupling of Tfa salt with Z-D (OMe)—I—P—OH in DMF with HOBT, HBTU DIEA and workup produced a crude product which was purified by column chromatography over silica gel. Elution with EtOAC: MeOH 95:5 gave pure fractions which were mixed and dried. Crystallization with EtOAC/Hexane, filtration and drying produced the pure product.

Animals. Time-pregnant C57/bL mice were housed under standard conditions: constant temperature (22±1° C.), humidity (relative, 30%) and a 12-h light/dark cycle with free access to food and water. The animals and protocol procedures were approved and supervised by the Committee on Animal Care (COAC) at Iowa State University.

Cell culture. Rat mesencephalic dopaminergic neuronal (N27) cells were cultured as described earlier (Anantharam et al., 2002). Briefly, cells were grown in RPMI 1640 medium containing 10% fetal bovine serum, 2 mM L-glutamine, 50 units of penicillin, and 50 μg/ml streptomycin. Cells were maintained in a humidified atmosphere of 5% $CO_2$ at 37° C. Primary mesencephalic neuronal cultures were prepared from the ventral mesencephalon of gestational 18-day-old mice embryos as described previously (Yang et al., 2004). Mesencephalic tissues were dissected and maintained in ice-cold $Ca_{2+}$-free HBSS and then dissociated in HBSS solution containing trypsin-EDTA (0.25%) for 20 min at 37° C. The dissociated cells were then plated at equal density (0.5×$10_6$ cells) in 30-mm-diameter tissue culture wells pre-coated with poly-lysine (1 mg/ml). Cultures were maintained in a chemically defined, serum-free medium consisting of neurobasal medium fortified with B-27 supplements, L-glutamine (500 μM), penicillin (100 IU/ml), and streptomycin (100 μg/ml) (Life Technologies). The cells were maintained in a humidified $CO_2$ incubator (5% $CO_2$, 37° C.) for 24 hr and then treated with cytosine arabinoside (10 μM) for 24 hr to inhibit glial cell proliferation. Half of the culture medium was replaced every 2 days. Approximately 6-7-day-old cultures were used for experiments.

Treatment paradigm. N27 and primary mesencephalic neurons were exposed to either 10-100 μM 6-OHDA or 10-300 μM $MPP^+$ in the presence or absence of 1-50 μM z-DIPD-fmk (SEQ ID NO:5) or z-DEVD-fmk (SEQ ID NO:6) for the duration of the experiment. DMSO (0.01%) was used as the vehicle control. Untreated or vehicle treated cells were used as control samples.

Cytotoxicity assays. N27 cells were incubated with 100 μM 6-OHDA for 24 hr or 300 μM $MPP^+$ for 36 hr in the presence or absence of 50 μM Z-DIPD-FMK (SEQ ID NO:5) and cell death was determined by MTT (3-(4,5-dimethylthiazol-3-yl)-2,5-diphenyl tetrazolium bromide) assay, which is widely used to assess cell viability (Kitazawa et al., 2001). After treatment, the cells were incubated in serum-free medium containing 0.25 mg/ml MTT for 3 hr at 37° C. Formation of formazan from tetrazolium was measured at 570 nm with a reference wavelength at 630 nm using a SpectraMax microplate reader (Molecular Devices, Sunnyvale, Calif.).

Caspase activity assay: Caspase-3 activity was measured using fluorescent based substrate as described earlier (Kaul et al., 2003). After treatment, the cells were resuspended in lysis buffer (50 mM Tris HCl, 1 mM EDTA, and 10 mM EGTA) containing 10 mM digitonin for 20 min at 37° C. Supernatants were treated with the fluorogenic substrate Ac-DEVD-AFC (SEQ ID NO:6) for caspase-3 for 1 hr at 37° C. and fluorescence was measured at excitation at 400 nm and emission at 505 nm using a fluorescence plate reader (Molecular Devices Inc.).

Western blotting. Cell lysates containing equal amounts of protein were loaded in each lane and separated on a 10-12% SDS-PA GE gel as described previously (Kaul et al., 2003).

After separation, proteins were transferred to nitrocellulose membrane, and nonspecific binding sites were blocked by treating with 5% nonfat dry milk powder. The membranes were then treated with primary antibodies directed against PKC (rabbit polyclonal or mouse monoclonal, 1:2000 dilution). The primary antibody treatments were followed by treatment with secondary HRPconjugated anti-rabbit IgG (1:2000) for 1 hr at RT. Secondary antibody-bound proteins were detected using Amersham's ECL chemiluminescence kit. To confirm equal protein loading, blots were reprobed with a β-actin antibody (1:5000 dilution). Western blot images were captured with a Kodak 2000 mM imaging system and data were analyzed using 1D Kodak imaging analysis software.

Immunoprecipitation kinase assay. PKCδ enzymatic activity was determined using immunoprecipitation as previously described (Kaul et al., 2003). N27 cells were treated with 100 μM 6-OHDA for 24 hr or 300 μM MPP$^+$ for 36 hr in the presence or absence of 50 μM z-DIPD-fmk (SEQ ID NO:5. After treatment, cell lysates were immunoprecipitated with anti-PKCδ antibody, 25 μl samples containing PKCδ bound to sepharose A beads were incubated with 25 μl of reaction buffer containing 0.4 mg histone H1 and 5 μCi of [$^{-32}$P] ATP (4,500 Ci/mM) for 10 min at 30° C. The reaction was terminated by the addition of 2×SDS gel loading buffer and boiled for 5 min. The samples were separated on 12.5% SDS-PAGE and histone phosphorylated bands were detected using a Phospho Imager (Personal Molecular Imager FX, Bio-Rad Laboratories, Hercules, Calif.) and quantified using Quantity One 4.2.0 Software (Bio-Rad Laboratories).

DNA fragmentation assay. DNA fragmentation assays were performed using a Cell Death Detection ELISA Plus Assay Kit, which is fast, highly sensitive and reliable for the detection of early changes in apoptotic cell death (Anantharam et al., 2002). DNA fragmentation was measured in N27 cells exposed to 100 μM 6-OHDA for 24 hr or 300 μM MPP$^+$ for 36 hr. Inhibition studies were performed in the presence or absence of 1-50 μM z-DEVD-fmk (SEQ ID NO:6 or 1-50 μM z-DIPD-fmk (SEQ ID NO:5). After treatments, 20 μl of cell lysate was processed according to the manufacturer's protocol. The assay solution consisted of a mixture of anti-histone biotin and anti-DNA-HRP directed against various histones and antibodies to both single stranded DNA and double stranded DNA, the major constituents of nucleosomes. After 2 hr of incubation, unbound components were removed by washing with the incubation buffer supplied with the kit. Quantification of the nucleosomes retained by anti-DNA-HRP in the immunocomplex was determined spectrophotometrically with ABTS (2,2'-azino-di[3-ethoxybenzyl thiazoline sulfonate) as an HRP substrate (supplied with the kit). Measurements were made at 405 nm against an ABTS solution as a blank (reference wave length 490 nm).

Immunocytochemistry. Immunostaining of the tyrosine hydroxylase (TH) marker of dopaminergic neurons was performed in primary mesencephalic neurons derived from C57 black mice (Yang et al., 2004). Briefly, cells were grown on poly-L-Lysine-coated glass cover slips. After treatment, the cells were fixed with 4% paraformaldehyde, permeabilized, and nonspecific sites were blocked with 5% normal goat serum containing 0.4% BSA and 0.2% Triton-X 100 in PBS for 20 min. Cells were then incubated with antibodies directed against TH (1:500 dilution) overnight at 4° C. followed by incubation with Cy3-conjugated (1:1000) secondary antibody for 1 hr at RT. Then the cover slips containing cells were washed with PBS, mounted on a slide, viewed under a Nikon inverted fluorescence microscope (Model TE-2000U) and images were captured with a SPOT digital camera (Diagnostic Instruments, Sterling Heights, Mich.).

Quantification of TH$_+$ cell count and neuronal processes. We will use Metamorph software (Universal Imaging, Version 5.0) for measurement of TH$_+$ cells and neuronal processes in primary neurons. For measurement of TH cell count, the images will first be thresholded, and then neuronal count and volume will be measured using the Integrated Morphometry Analysis (IMA) function. The data will be logged to an Excel spreadsheet with defined row and column positions and then analyzed. For measurement of neuronal processes, the length of the processes will be marked by applying the region and length measurement function in the IMA. The data will be exported to an Excel spreadsheet and analyzed. TH$_+$ neurons and their processes will be counted in at least six individual cultures for each treatment. This method is a modified version of methodology recently used for quantification of neuronal processes (Klimaschewski et al., 2002; Jones et al., 2004).

Development of DMQD (SEQ ID NO:7) and DMQA (SEQ ID NO:8) lentiviral constructs and determination of neuroprotective effect in a cell culture model of PD. Oligonucleotides that express a triple tandem human PKCδ cleavage motif (AGEDMQDNSG (SEQ ID NO:2), DMQD (SEQ ID NO:7) peptide) or cleavage-resistant human PKCδ cleavage motif (AGEDMQANSG (SEQ ID NO:4), DMQA (SEQ ID NO:8) peptide) were first chemically synthesized. The pLenti/TOPO Lentiviral gene expression system (Invitrogen, Carlsbad, Calif.) was employed for the expression of DMQD (SEQ ID NO:7) or DMQA (SEQ ID NO:8) in N27 cells. Briefly, after annealing, these duplex oligonucleotides were directly cloned into pLenti/TOPO to generate pLentiD/TOPO and pLentiA/TOPO. To produce the lentivirus that contains pLentiD/TOPO or pLentiA/TOPO, individual pLentiD/TOPO or pLentiA/TOPO constructs as well as supporting plasmids (supplied with the kit) were transfected into human 293FT cells with the use of lipofectamine 2000, as described in the kit's instructions. The lentivirus in the medium was collected by centrifuging at 1500×g for 15 min, 48-72 hr post-transfection. To generate a stably expressing cell line, lentiviral particles containing pLentiD/TOPO or pLentiA/TOPO constructs were added into cultured N27 cells (2×105) followed by polybrene (6 μg/ml) and incubated for 24 hr and replaced with fresh medium. Positive N27 cells were selected by keeping blasticidin (10 μg/ml) in medium for up to 2 weeks. DMQD (SEQ ID NO:7) or DMQA (SEQ ID NO:8) expressing N27 cells were identified by immunostaining of the Cterminal V5 epitope. These cells were treated with MPP$^+$ or 6-OHDA and then cytotoxicity was measured by the Sytox staining method (Sun et al., 2005).

Data analysis. Data analysis was performed using Prism 3.0 software (GraphPad Software, San Diego, Calif.). Data were first analyzed using one-way ANOVA. Bonferroni's post-test was then performed to compare all groups, and differences with $p<0.05$ were considered significant.

Results

Design and synthesis of PKCδ cleavage inhibitor z-DIPD-fmk. Several studies have implicated oxidative insult, mitochondrial dysfunction, caspases and apoptotic cell death in development of various neurodegenerative disorders. We have recently established PKCδ as a key proapoptotic molecule in oxidative stress-mediated neurodegenerative processes (Kanthasamy et al., 2003) and therefore, the kinase may serve as an attractive target of pharmacological intervention. To develop a cell permeable peptide inhibitor to specifically block PKCδ cleavage, we chose the peptide Asp-Ile-Pro-Asp (z-DIPD-fmk) (SEQ ID NO:5) corresponding to position 324-237 in rat PKCδ cDNA directed against the caspase-3 cleavage site of PKCδ (Kanthasamy et al., 2003). The cell permeable z-DIPD-fmk (SEQ ID NO:5) was synthesized as described in the methods section. Functional characterization of z-DIPD-fmk (SEQ ID NO:5), including neuroprotective effects, was conducted in cell culture models of PD.

Figure 7A:
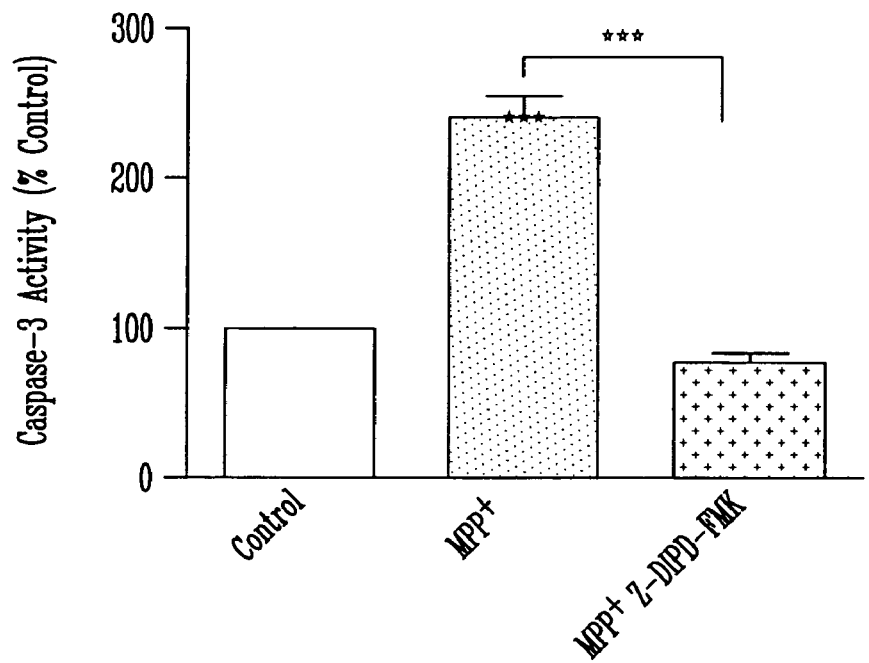
FIGS. 7A and 7B are graphs demonstrating the effect of z-DIPD-fmk (SEQ ID NO:5) on MPP$^+$- and 6-OHDA-induced caspase-3 activation. Asterisks (*Kanthasamy et al., 2005 26 $p<0.05$ or **$p<0.01$) indicate significant difference compared with control cells and pound sign (# $p<0.05$ or ## $p<0.01$) indicates significant differences between z-DIPD-fmk (SEQ ID NO:5-co-treated and MPP$^+$ or 6-OHDA treated cells.
Figure 7B:
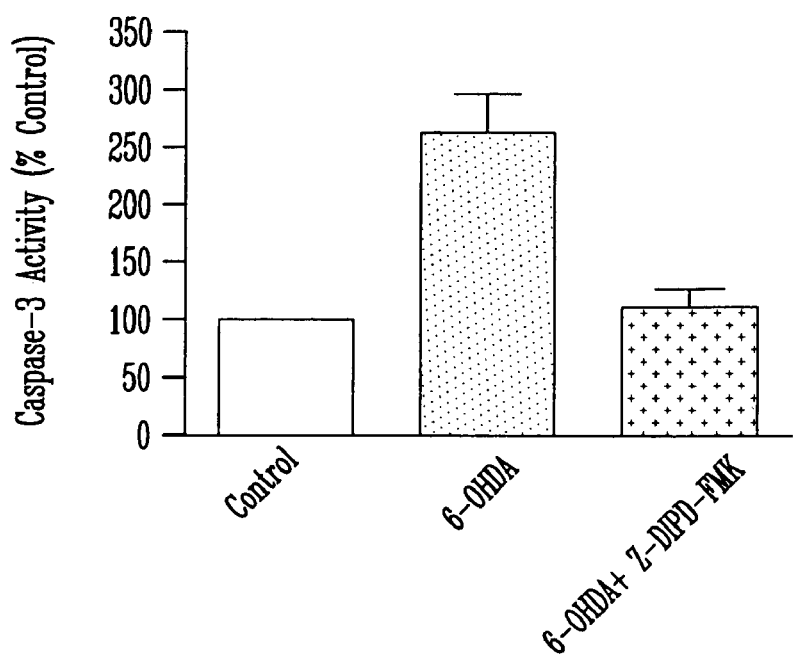

Neuroprotective effect of z-DIPD-fmk (SEQ ID NO:5) on $MPP^+$- and 6-OHDA-induced dopaminergic cell death. We previously showed that caspase-3 and proteolytically activated PKCδ mediate $MPP^+$-induced cytotoxic cell death in N27 dopaminergic clonal neuronal cells (Kaul et al., 2003). In this experiment, we examined the effect of the PKCδ cleavage inhibitor z-DIPD-fmk (SEQ ID NO:5) on $MPP^+$-induced cytotoxic cell death. As shown in FIG. 2A, N27 cells were exposed to either $MPP^+$ in the absence or presence of z-DIPD-fmk (SEQ ID NO:5) and cell viability was determined by MTT assay. Exposure to 300 μM $MPP^+$ for 36 hr resulted in the loss of cell viability by more than 40%, whereas cell viability was decreased by only 20% in cells treated with 50 μM z-DIPD-fmk (SEQ ID NO:5), suggesting that the PKCδ cleavage inhibitor significantly blocks $MPP^+$-induced cytotoxicity. To further confirm the protective effect of z-DIPD-fmk (SEQ ID NO:5) on another oxidative stress model of PD, we examined whether z-DIPD-fmk (SEQ ID NO:5) can also block the cytotoxic effect of the dopaminergic toxin 6-OHDA. FIG. 2B shows exposure of N27 cells to 100 μM 6-OHDA for 24 hr resulted in decreased cell viability by more than 60%, but z-DIPD-fmk (SEQ ID NO:5) (50 μM) treatment significantly protected against 6-OHDA-induced cell death, indicating that the PKCδ cleavage inhibitor z-DIPD-fmk (SEQ ID NO:5) displays a neuroprotective effect in both $MPP^+$- and 6-OHDA-induced cell models of PD.

z-DIPD-fmk (SEQ ID NO:5) caspase-3 activity in PD models. The effector cysteine protease caspase-3 is a mediator of neuronal apoptosis. Therefore, in this experiment we examined the effect of the PKCδ cleavage inhibitor z-DIPD-fmk (SEQ ID NO:5) on $MPP^+$- and 6-OHDA-induced caspase-3 activation. As shown in FIG. 3, N27 cells were exposed to either $MPP^+$ or 6-OHDA in the absence or presence of z-DIPD-fmk (SEQ ID NO:5) and then caspase-3 activity was determined by enzymatic assay. Exposure to 300 μM $MPP^+$ for 36 hr resulted in an ~2.5 fold increase in caspase-3 enzyme activity (FIG. 7A). Similarly, exposure to 100 μM 6-OHDA for 24 hr also resulted in an ~2.5 fold increase in caspase-3 enzyme activity (FIG. 7B). 50 μM z-DIPD-fmk (SEQ ID NO:5) completely blocked both $MPP^+$- and 6-OHDA-induced caspase-3 activation, demonstrating a potent antiapoptotic effect of z-DIPD-fmk (SEQ ID NO:5 in cell culture models of PD.

z-DIPD-fmk (SEQ ID NO:5) attenuates proteolytic action of PKCδ in PD models. We previously demonstrated that PKCδ is proteolytically activated by caspase-3 in $MPP^+$ and 6-OHDA models (Kaul et al., 2003; Kanthasamy et al., 2003). Because z-DIPD-fmk (SEQ ID NO:5) was designed to competitively block the caspase-3 cleavage site 324DIPD327 (SEQ ID NO:5), we tested the efficacy of the peptide against $MPP^+$- and 6-OHDA-induced PKCδ cleavage in N27 cells. Exposure of N27 cells to 300 μM $MPP^+$ for 36 hr induced proteolytic cleavage of PKCδ (72-74 kDa) into 38-kDa regulatory and 41-kDa catalytically active fragments (FIG. 8A), whereas $MPP^+$-induced proteolytic cleavage of PKCδ was almost completely attenuated by co-incubation with 50 μM z-DIPD-fmk (SEQ ID NO:5). Similarly, treatment with 100 μM 6-OHDA for 24 hr also resulted in proteolytic cleavage of PKCδ, which was significantly attenuated by z-DIPD-fmk (SEQ ID NO:5) (50 μM) co-treatment (FIG. 8A).

Figure 9A:
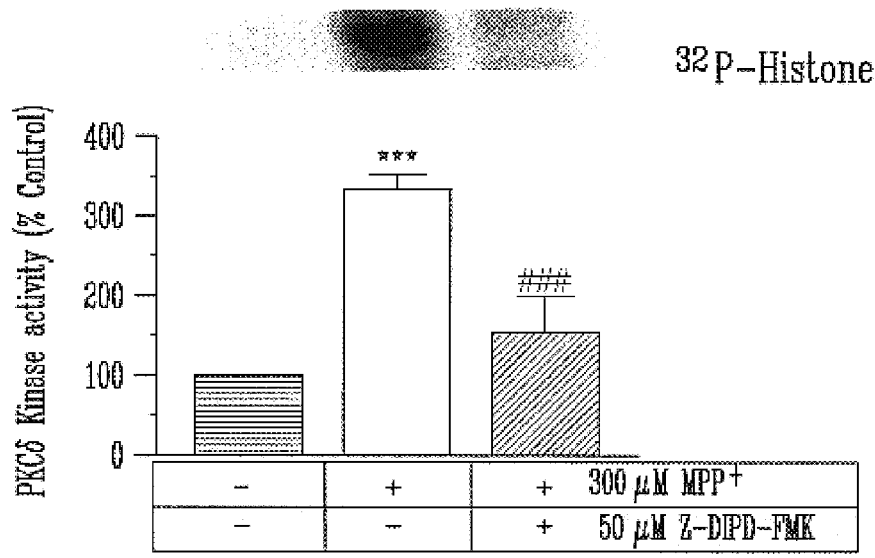
FIGS. 9A and 9B show the effect of z-DIPD-fmk (SEQ ID NO:5) on MPP$^+$- and 6-OHDA-induced PKCδ kinase activity. PKCδ kinase activity in Western blot of A., MPP$^+$±z-DIPD-fmk (SEQ ID NO:5) treated cells and B, 6-OHDA±z-DIPD-fmk (SEQ ID NO:5) treated cells. The values represent mean±SEM from two separate experiments performed in duplicate. Asterisks (*p<0.05 or **p<0.01) indicate significant difference compared with control cells and pound sign (# p<0.05 or ## p<0.01) indicates significant differences between z-DIPD-fmk (SEQ ID NO:5)-co-treated and MPP$^+$ or 6-OHDA treated cells. Kanthasamy et al., 2005

We further tested whether z-DIPD-fmk (SEQ ID NO:5) can also attenuate 6-OHDA-induced increases in PKCδ enzyme activity. Immunoprecipitation kinase assay was performed in N27 cells by measuring PKCδ phosphorylation of histone H1 using [32P]-ATP. Exposure to 300 μM $MPP^+$ for 36 hr resulted in a 333% increase in PKCδ enzymatic activity over the untreated cells (FIG. 9A). Co-treatment with 50 μM z-DIPD-fmk (SEQ ID NO:5) almost completely suppressed the $MPP^+$-induced kinase activity. Similarly, exposure to 100 μM 6-OHDA for 24 hr resulted in a 235% increase in PKCδ enzymatic activity over the untreated cells (FIG. 5B). Co-treatment with 50 μM z-DIPD-fmk (SEQ ID NO:5) also almost completely suppressed the 6-OHDA-induced kinase activity. Together, these data indicate that z-DIPD-fmk (SEQ ID NO:5) significantly suppresses $MPP^+$- and 6-OHDA-induced PKCδ proteolytic activation.

Figure 10A:
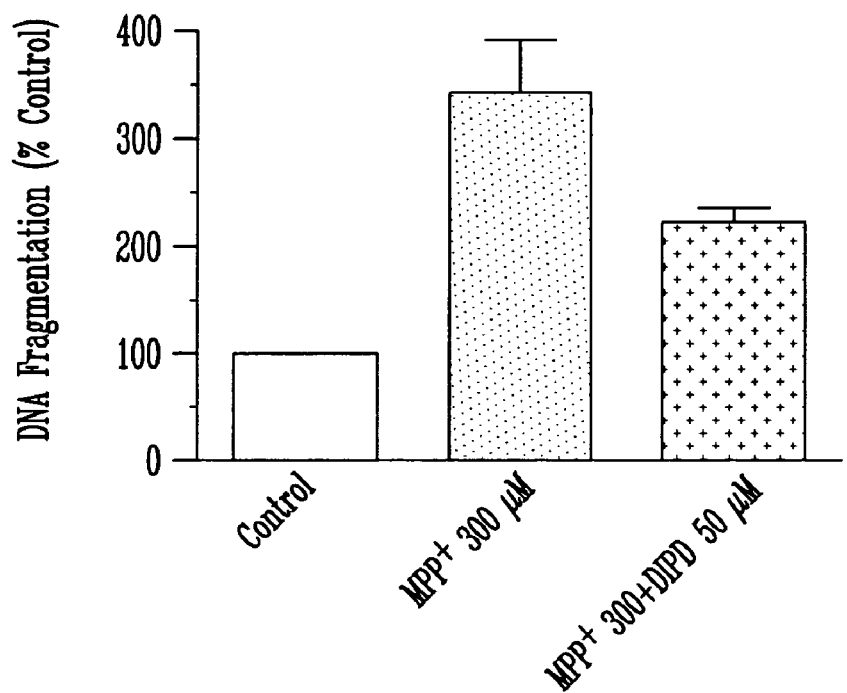
FIGS. 10A and 10B show the effect of z-DIPD-fmk (SEQ ID NO:5) on MPP$^+$- and 6-OHDA-induced apoptotic cell death. DNA fragmentation in A., MPP$^+$±z-DIPD-fmk (SEQ ID NO:5) treated cells and B, 6-OHDA±z-DIPD-fmk (SEQ ID NO:5) treated cells. Each bar represents mean±SEM for n=6-9. Asterisks (*p<0.05 or **p<0.01) indicate significant difference compared with control cells and pound sign (# p<0.05 or ## p<0.01) indicates significant differences between z-DIPD-fmk (SEQ ID NO:5-co-treated and MPP$^+$ or 6-OHDA treated cells.
Figure 12A:
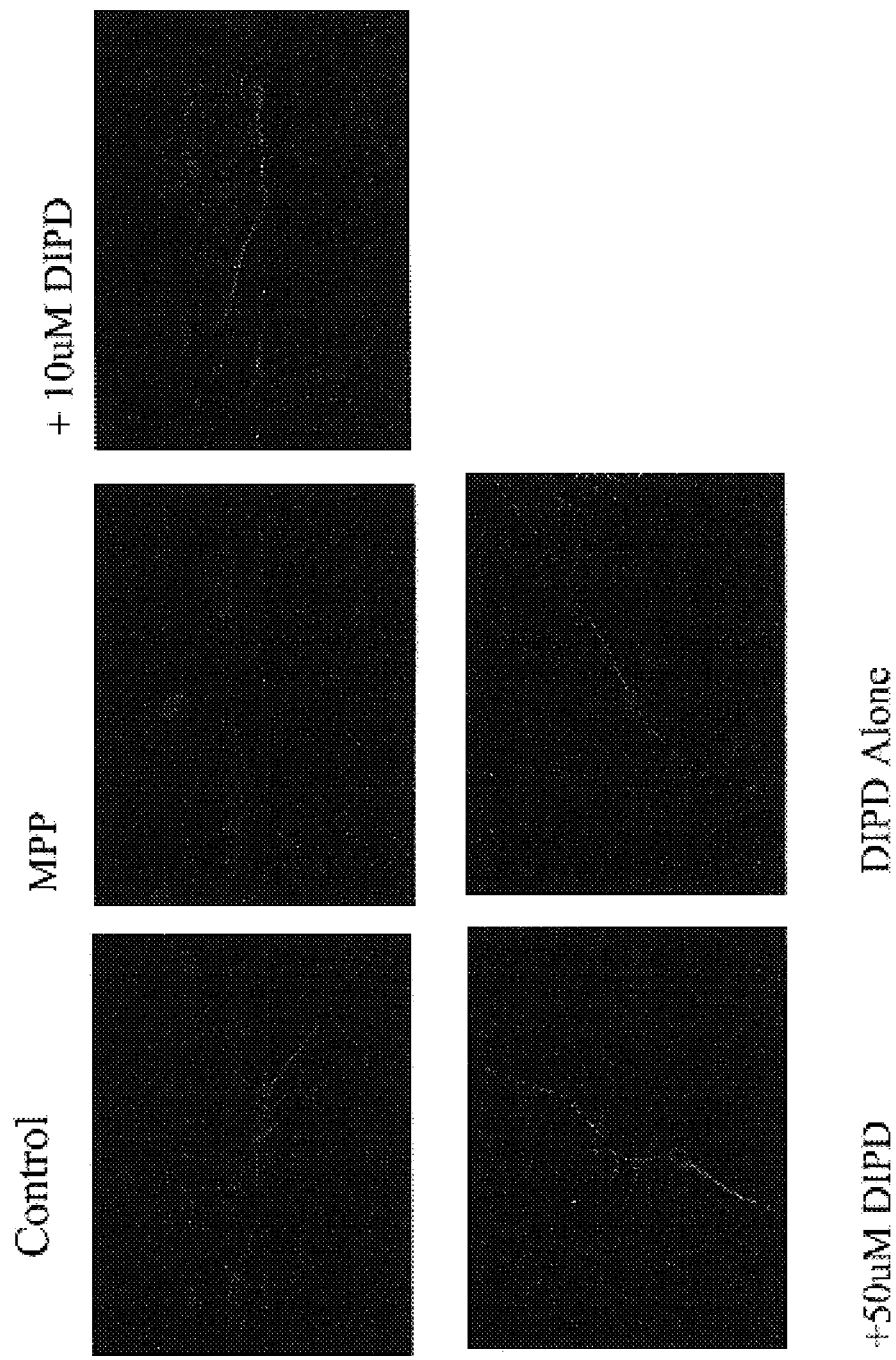
Figure 12B:
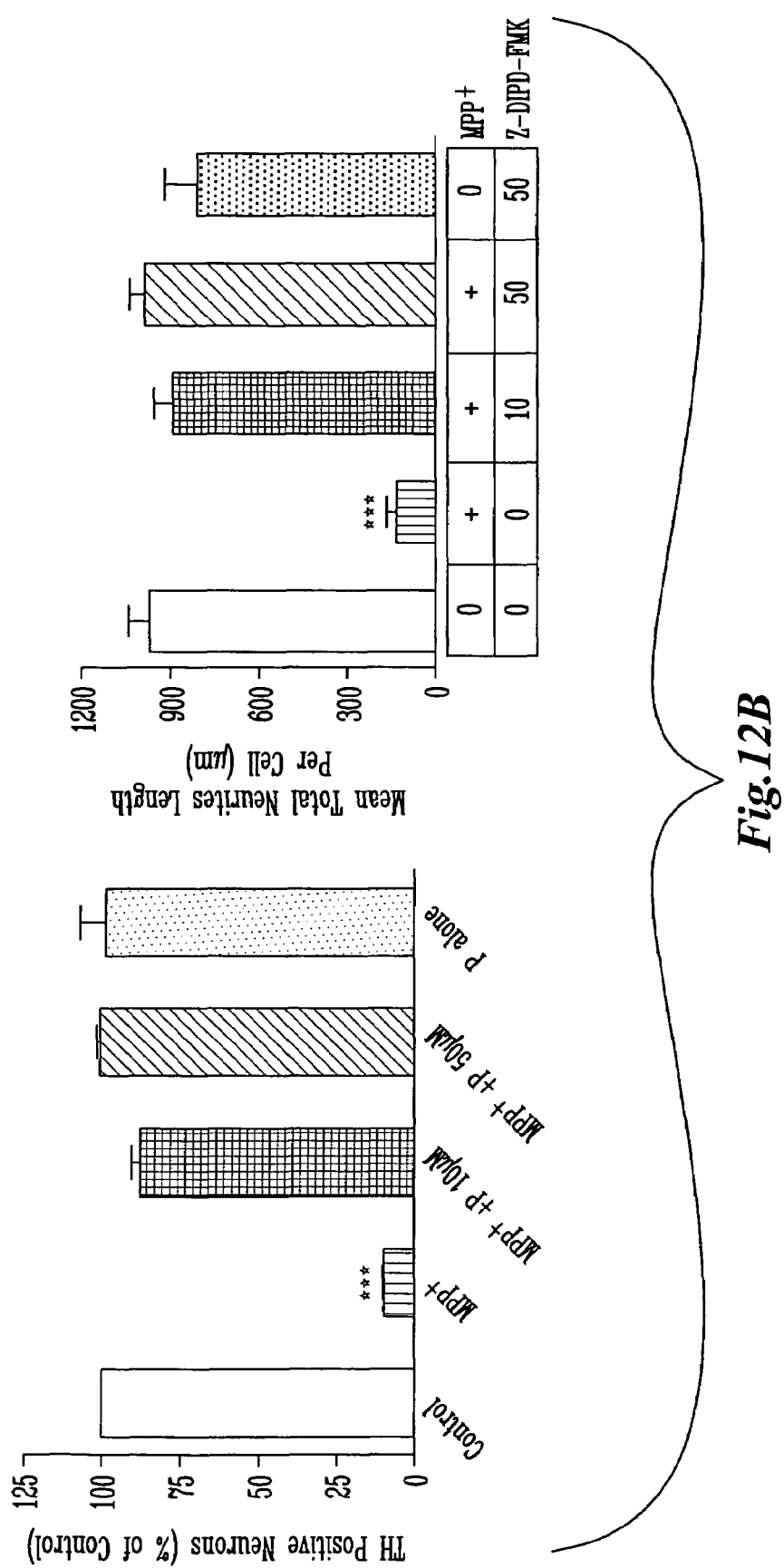
Figure 12D:
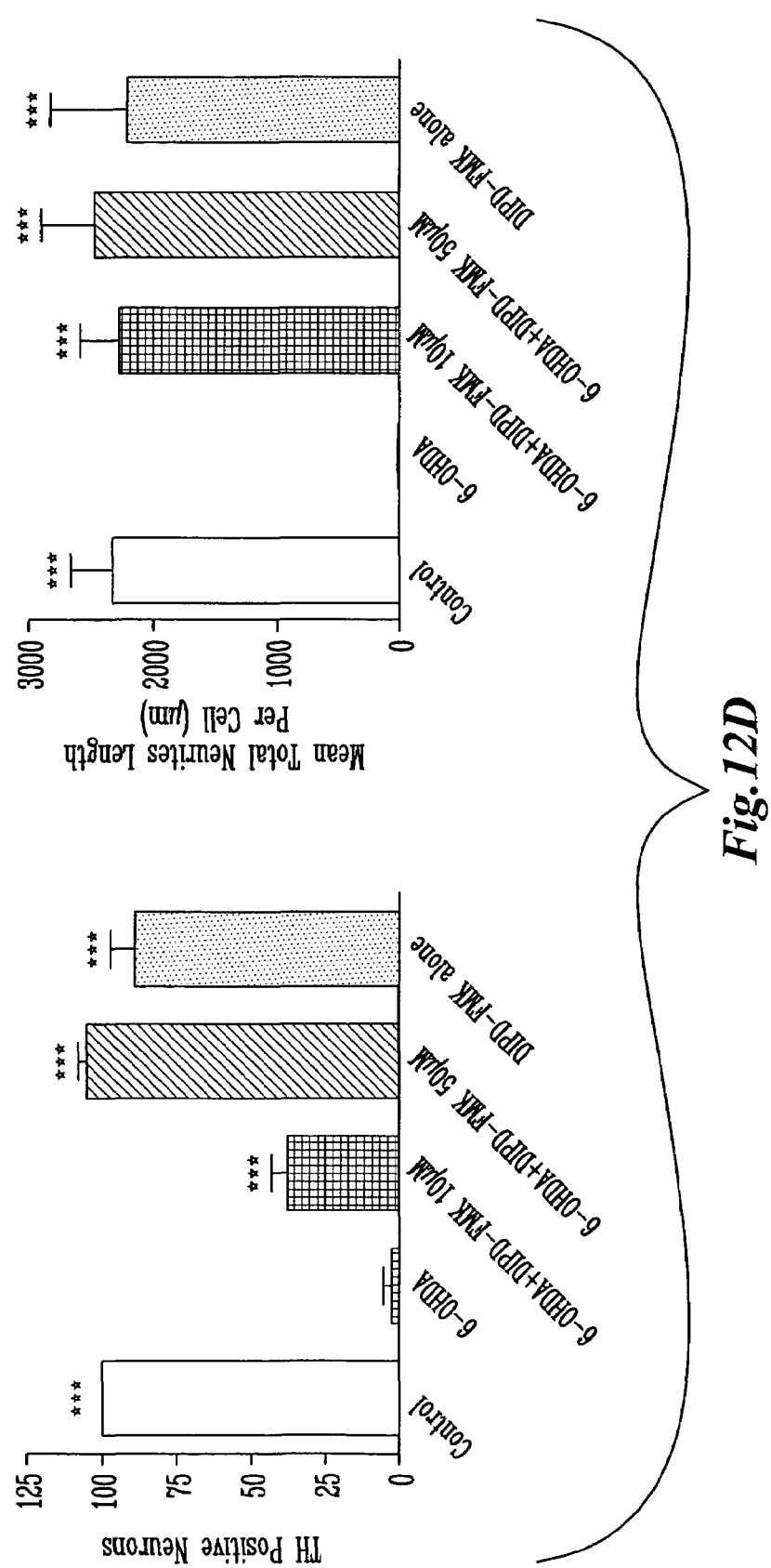

Antiapoptotic effect of z-DIPD-fmk (SEQ ID NO:5) in $MPP^+$- and 6-OHDA-models of PD. Chromosomal breakdown of DNA into 200-base pair nucleosomal fragments and DNA condensation are hallmarks of cellular apoptosis (Cohen, 1997). We recently showed that both $MPP^+$ and 6-OHDA induced apoptotic cell death qualitatively and quantitatively in N27 cells (Kaul et al., 2003). Further, we also demonstrated caspase-3-mediated proteolytic activation is essential for induction of apoptotic cell death in PD models (Kaul et al., 2003; Yang et al., 2004). Therefore, we examined the effect of z-DIPD-fmk (SEQ ID NO:5) on $MPP^+$- and 6-OHDA-induced apoptotic cell death. To quantify apoptotic cell death, we used an ELISA DNA fragmentation assay which measures cytoplasmic low molecular weight histone-associated DNA (Kaul et al., 2003). Exposure to 300 μM $MPP^+$ for 36 hr and 100 μM 6-OHDA for 24 hr caused an increase in DNA fragmentation by 75% and 93% compared to untreated cells, respectively (FIG. 10). z-DIPD-fmk (SEQ ID NO:5) (50 μM) significantly attenuated $MPP^+$-induced DNA fragmentation (FIG. 10A). Similarly, co-treatment with 50 μM z-DIPD-fmk (SEQ ID NO:5) also completely blocked 6-OHDA-induced DNA fragmentation in N27 cells (FIG. 6B). To compare the efficacy of z-DIPD-fmk (SEQ ID NO:5) with that of the known caspase-3 inhibitor z-DEVD-fmk (SEQ ID NO:6), we performed a dose-response study on 6-OHDA-induced apoptotic cell death. N27 cells were first incubated with either 1-50 μM z-DIPD-fmk (SEQ ID NO:5) or 1-50 μM z-DEVD-fmk (SEQ ID NO:6) and then exposed to 100 μM 6-OHDA for 24 hr. Both z-DIPD-fmk (SEQ ID NO:5) and z-DEVD-fmk (SEQ ID NO:6) dose dependently blocked 6-OHDA-induced apoptotic cell death. Dose-response analysis revealed an $IC_{50}$ of 6 μM for z-DIPD-fmk (SEQ ID NO:5) and an $IC_{50}$ of 18 μM for z-DEVD-fmk (SEQ ID NO:6), indicating that the novel PKCδ cleavage inhibitor z-DIPD-fmk (SEQ ID NO:5) is at least 3 times more potent than the widely used caspase-3 inhibitor z-DEVD-fmk (SEQ ID NO:6) at protecting against 6-OHDA-induced apoptotic cell death.

z-DIPD-fmk (SEQ ID NO:5) rescues $MPP^+$- and 6-OHDA-induced TH+ neuronal loss in primary mesencephalic cultures. Next we extended our studies from N27 dopaminergic clonal cells to primary neuronal cultures. We characterized the neuroprotective effect of z-DIPD-fmk (SEQ ID NO:5) against $MPP^+$- and 6-OHDA-induced dopaminergic neuronal degeneration in primary nigral dopaminergic neuronal cultures. Primary mesencephalic dopaminergic neuronal cells were exposed to 10 μM MPP⁺ in the presence or absence of z-DIPD-fmk (SEQ ID NO:5) (10 and 50 μM). After 24 hr exposure, primary neurons were fixed and stained for TH. The number of TH+ cells as well as their neurite length was quantified. As shown in FIG. 12A, z-DIPD-fmk (SEQ ID NO:5) significantly blocked MPP⁺-induced degeneration of TH+ neurons and their processes in primary nigral dopaminergic neurons. Quantitative analysis of TH+ cell counts showed nearly complete protection against MPP⁺ neurotoxicity (FIG. 12B). The average lengths of TH+ neuronal processes in MPP⁺ plus z-DIPD-fmk (SEQ ID NO:5) treated cells were significantly longer than the processes of neurons treated only with MPP⁺ (FIG. 12B). Similarly, primary nigral dopaminergic neurons were exposed to 30 μM 6-OHDA in the presence or absence of z-DIPD-fmk (SEQ ID NO:5) (10 and 50 μM). As shown in FIG. 12C, z-DIPD-fmk (SEQ ID NO:5) significantly blocked 6-OHDA-induced degeneration of TH+ neurons and their processes in primary nigral cultures. Quantitative analysis of TH+ cell counts consistently showed nearly complete protection against 6-OHDA neurotoxicity (FIG. 12D). Collectively, these results clearly demonstrate the neuroprotective effect of z-DIPD-fmk (SEQ ID NO:5) in dopaminergic neurodegenerative models.

Expression of PKCδ cleavage site peptide in dopaminergic neuronal cells and determination of neuroprotective effect. We developed lentiviral constructs that express the triple tandem human PKCδ cleavage motif (AGEDMQDNSG (SEQ ID NO:2), DMQD (SEQ ID NO:7) peptide) or cleavage-resistant human PKCδ cleavage motif (AGEDMQANSG (SEQ ID NO:4), DMQA (SEQ ID NO:8) peptide) by cloning the sequence in the pLenti/TOPO Lentiviral gene expression system (Invitrogen, Carlsbad, Calif.). These constructs were transfected into N27 cells and the neuroprotective effect was determined by Sytox staining. As shown in FIG. 13, both DMQD (SEQ ID NO:7) and DMQA (SEQ ID NO:8) expressing cells were more resistant to MPP⁺- and 6-OHDA-induced cell death compared to vector control cells. Thus, expression of the PKCδ cleavage peptide in neuronal cells via viral vectors can afford neuroprotection.

Discussion

The present study demonstrates that the cell permeable inhibitor z-DIPD-fmk (SEQ ID NO:5) directed against the PKCδ caspase-3 cleavage site protects dopaminergic neurons from MPP⁺- and 6-OHDA-induced apoptotic cell death. Notably, z-DIPD-fmk (SEQ ID NO:5) effectively blocked caspase-3 dependent proteolytic activation of PKCδ and DNA fragmentation in cell culture models of PD. The neuroprotective effect of the PKCδ cleavage site inhibitor peptide was also evident against dopaminergic neurodegeneration, as the inhibitor completely rescued TH+ neurons from MPP⁺- and 6-OHDA-induced neurotoxicity. To our knowledge, this is the first report demonstrating a neuroprotective strategy using the peptide inhibitor directed against the PKCδ cleavage site in a cell culture model of Parkinson's disease.

Oxidative stress and apoptotic cell death have been implicated in several neurodegenerative disorders including Parkinson's disease (Allam et al., 2005; Maguire-Zeiss et al., 2005; West et al., 2005). Recently, we demonstrated that PKC is an oxidative stress sensitive kinase in cell culture and animal models of Parkinson's disease (Kanthasamy et al., 2003; Kaul et al., 2003; Kitazawa et al., 2003; Anantharam et al., 2004; Yang et al., 2004). Oxidative stress activates PKCδ, a member of the novel PKC family, by proteolysis in which caspase-3 cleaves the native kinase (72-74-kDa) at the 324DIPD327 (SEQ ID NO:5)-site, resulting in 41-kDa catalytically active and 38-kDa regulatory fragments, to persistently activate the kinase (Kanthasamy et al., 2003; Kaul et al., 2005a). The cleavage site is strategically located at the hinge where the regulatory domain and catalytic domain are joined and therefore, the cleavage at this site results in persistently active catalytic fragments. We recently showed that phosphorylation of PKCδ at tyrosine residue 311 is essential for the proteolytic cleavage of the kinase during oxidative stress (Kaul et al., 2005b).

The proteolytic activation of PKCδ plays a key role in promoting apoptotic cell death in various cell types including neuronal cells (Kikkawa et al., 2002; Brodie and Blumberg, 2003; Kanthasamy et al., 2003). Attenuation of PKCδ proteolytic activation by antioxidants suggests that the cellular redox status can influence activation of the proapoptotic kinase (Kaul et al., 2003). Pharmacological inhibitors that block the MPT pore as well as the mitochondrial dependent caspase cascade attenuate proteolytic activation of PKCδ (Kaul et al., 2003; Kitazawa et al., 2005). Reduced cellular antioxidant capacity, increased oxidative stress and impaired mitochondrial function are clearly associated with development of PD (Beal, 2003; Dawson and Dawson, 2003; Fiskum et al., 2003; Greenamyre and Hastings, 2004; Hald and Lotharius, 2005). Overexpression of loss of function dominant negative mutant $PKC\delta_{D327A}$ (caspase-cleavage resistant), $PKC\delta_{K376R}$ (kinase inactive) and $PKC\delta_{Y311F}$ (phosphorylation defective) proteins also attenuate dopaminergic neurons from MPP⁺ and oxidative stress-induced apoptotic cell death (Kaul et al., 2003; Kitazawa et al., 2003; Anantharam et al., 2004; Kaul et al., 2005b; Latchoumycandane et al., 2005). The critical role of PKCδ in mediating neuronal apoptosis was demonstrated in RNAi studies. Suppression of caspase-3 dependent proteolytic activation of PKCδ by small interfering RNA (siRNA) prevents MPP⁺-induced dopaminergic degeneration (Yang et al., 2004). In addition to the proapoptotic role, PKCδ may also amplify apoptotic signaling via positive feedback activation of the caspase cascade (Anantharam et al., 2002; Kaul et al., 2003; Kitazawa et al., 2003). Thus, the dual role of PKCδ as a mediator and amplifier of apoptosis may be important in the pathogenesis of major neurodegenerative disorders such as Parkinson's disease, Alzheimer's disease, and Huntington disease. Together, our results suggest that the proapoptotic PKCδ is a valid pharmacological target for development of a neuroprotective strategy against oxidative stress-induced dopaminergic degeneration in Parkinson's disease.

A number of studies are underway to develop neuroprotective agents to target cell death signaling molecules. For example, the mixed lineage kinase (MLK) inhibitor CEP-1347 has been tested in animal models of PD (Johnston and Brotchie, 2004; Wang et al., 2004; Kuan and Burke, 2005; Silva et al., 2005) and is currently being evaluated in human clinical trials (Phase II and III). Also, Poly-ADP-ribose polymerase (PARP) inhibitor has been shown to protect nigral dopaminergic neurons in animal models (Cosi et al., 1996; Iwashita et al., 2004). Since PKCδ has been shown to indirectly regulate PARP and MLK (Merritt et al., 1999; Yoshida et al., 2002; Kitazawa et al., 2004), PKCδ inhibitor may be an attractive neuroprotective therapeutic target.

Therapeutic intervention to inhibit PKCδ function is not currently possible because a specific inhibitor for this enzyme has not been identified. Currently, rottlerin, a natural compound from the medicinal tree *Mallotus philippinensis*, is used often as a specific inhibitor of PKCδ, but also appears to inhibit other kinases such as casein kinase, CaM kinases, Src kinases and MAP kinases (Gschwendt, 1999; Reyland et al., 1999; Davies et al., 2000; Basu et al., 2001). In addition rottlerin has also been shown to directly uncouple mitochondrial respiration from oxidative phosphorylation (Soltoff, 2001). Because protein kinases play a diverse role in normal physiological function, an inhibitor that interferes with only abnormally activated kinase is urgently warranted. The PKCδ cleavage site inhibitor interferes with the proteolytically activated PKCδ but not with the native form and therefore, it is expected to produce only minimal side effects as compared to conventional kinase inhibitors. The lentiviral constructs expressing this cleavage site peptide are effective in cell culture models, and are under investigation in animal models.

In conclusion, we demonstrated that selective targeting of proteolytic activation of PKCδ with the novel cell permeable inhibitor z-DIPD-fmk (SEQ ID NO:5) can offer excellent neuroprotection against dopaminergic degeneration in cell culture models of Parkinson's disease.

All references, patents and the like cited herein are hereby expressly incorporated in their entirety by reference.

Allam M F, Del Castillo A S and Navajas R F (2005) Parkinson's disease risk factors: genetic, environmental, or both? *Neurol Res* 27:206-208.

Anantharam V, Kitazawa M, Latchoumycandane C, Kanthasamy A and Kanthasamy A G (2004) Blockade of PKC{delta} Proteolytic Activation by Loss of Function Mutants Rescues Mesencephalic Dopaminergic Neurons from Methylcyclopentadienyl Manganese Tricarbonyl (MMT)-Induced Apoptotic Cell Death. *Ann NY Acad Sci* 1035:271-289.

Anantharam V, Kitazawa M, Wagner J, Kaul S and Kanthasamy A G (2002) Caspase-3-dependent proteolytic cleavage of protein kinase Cdelta is essential for oxidative stress mediated dopaminergic cell death after exposure to methylcyclopentadienyl manganese tricarbonyl. *J Neurosci* 22:1738-1751.

Basu A, Woolard M D and Johnson C L (2001) Involvement of protein kinase C-delta in DNA damage-induced apoptosis. *Cell Death Differ* 8:899-908.

Beal M F (2003) Mitochondria, oxidative damage, and inflammation in Parkinson's disease. *Ann NY Acad Sci* 991:120-131.

Brodie C and Blumberg P M (2003) Regulation of cell apoptosis by protein kinase c delta. *Apoptosis* 8:19-27.

Cohen G M (1997) Caspases: the executioners of apoptosis. *Biochem J* 326 (Pt 1):1-16.

Cosi C, Colpaert F, Koek W, Degryse A and Marien M (1996) Poly(ADP-ribose) polymerase inhibitors protect against MPTP-induced depletions of striatal dopamine and cortical noradrenaline in C57B1/6 mice. *Brain Res* 729:264-269.

Davies S P, Reddy H, Caivano M and Cohen P (2000) Specificity and mechanism of action of some commonly used protein kinase inhibitors. *Biochem J* 351:95-105.

Dawson T M and Dawson V L (2003) Molecular pathways of neurodegeneration in Parkinson's disease. *Science* 302: 819-822.

Fiskum G, Starkov A, Polster B M and Chinopoulos C (2003) Mitochondrial mechanisms of neural cell death and neuroprotective interventions in Parkinson's disease. *Ann NY Acad Sci* 991:111-119.

Greenamyre J T and Hastings T G (2004) Biomedicine. Parkinson's—divergent causes, convergent mechanisms. *Science* 304:1120-1122.

Gschwendt M (1999) Protein kinase C delta. *Eur J Biochem* 259:555-564.

Hald A and Lotharius J (2005) Oxidative stress and inflammation in Parkinson's disease: is there a causal link? *Exp Neurol* 193:279-290.

Iwashita A, Yamazaki S, Mihara K, Hattori K, Yamamoto H, Ishida J, Matsuoka N and Mutoh S (2004) Neuroprotective effects of a novel poly(ADP-ribose) polymerase-1 inhibitor, 2-[3-[4-(4-chlorophenyl)-1-piperazinyl]propyl]-4 (3H)-quinazolinone (FR255595), in an in vitro model of cell death and in mouse 1-methyl-4-phenyl-1,2,3,6-tetrahydropyridine model of Parkinson's disease. *J Pharmacol Exp Ther* 309:1067-1078.

Johnston T H and Brotchie J M (2004) Drugs in development for Parkinson's disease. *Curr Opin Investig Drugs* 5:720-726.

Jones S B, Lu H Y and Lu Q (2004) Abl tyrosine kinase promotes dendrogenesis by inducing actin cytoskeletal rearrangements in cooperation with rho family small GTPases in hippocampal neurons. *J Neurosci* 24:8510-8521.

Kanthasamy A G, Kitazawa M, Kanthasamy A and Anantharam V (2003) Role of proteolytic activation of protein kinase Cdelta in oxidative stress-induced apoptosis. *Antioxid Redox Signal* 5:609-620.

Kaul S, Anantharam V, Kanthasamy A and Kanthasamy A G (2005a) Wild-type alpha-synuclein interacts with pro-apoptotic proteins PKCdelta and BAD to protect dopaminergic neuronal cells against MPP(+)-induced apoptotic cell death. *Brain Res Mol Brain Res* 139:137-152.

Kaul S, Anantharam V, Yang Y, Choi C J, Kanthasamy A and Kanthasamy A G (2005b) Tyrosine phosphorylation regulates the proteolytic activation of protein kinase Cdelta in dopaminergic neuronal cells. *J Biol Chem* 280:28721-28730.

Kaul S, Kanthasamy A, Kitazawa M, Anantharam V and Kanthasamy A G (2003) Caspase-3 dependent proteolytic activation of protein kinase C delta mediates and regulates 1-methyl-4-phenylpyridinium (MPP$^+$)-induced apoptotic cell death in dopaminergic cells: relevance to oxidative stress in dopaminergic degeneration. *Eur J Neurosci* 18:1387-1401.

Kikkawa U, Matsuzaki H and Yamamoto T (2002) Protein kinase C delta (PKC delta): activation mechanisms and functions. *J Biochem (Tokyo)* 132:831-839.

Kitazawa M, Anantharam V, Kanthasamy A and Kanthasamy A G (2004) Dieldrin promotes proteolytic cleavage of poly (ADP-ribose) polymerase and apoptosis in dopaminergic cells: protective effect of mitochondrial anti-apoptotic protein Bcl-2. *Neurotoxicology* 25:589-598.

Kitazawa M, Anantharam V and Kanthasamy A G (2001) Dieldrin-induced oxidative stress and neurochemical changes contribute to apoptopic cell death in dopaminergic cells. *Free Radic Biol Med* 31:1473-1485.

Kitazawa M, Anantharam V and Kanthasamy A G (2003) Dieldrin induces apoptosis by promoting caspase-3-dependent proteolytic cleavage of protein kinase Cdelta in dopaminergic cells: relevance to oxidative stress and dopaminergic degeneration. *Neuroscience* 119:945-964.

Kitazawa M, Anantharam V, Yang Y, Hirata Y, Kanthasamy A and Kanthasamy A G (2005) Activation of protein kinase C delta by proteolytic cleavage contributes to manganese induced apoptosis in dopaminergic cells: protective role of Bcl-2. *Biochem Pharmacol* 69:133-146.

Klimaschewski L, Nindl W, Pimpl M, Waltinger P and Pfaller K (2002) Biolistic transfection and morphological analysis of cultured sympathetic neurons. *J Neurosci Methods* 113: 63-71.

Kuan C Y and Burke R E (2005) Targeting the JNK signaling pathway for stroke and Parkinson's diseases therapy. *Curr Drug Targets CNS Neurol Disord* 4:63-67.

Latchoumycandane C, Anantharam V, Kitazawa M, Yang Y, Kanthasamy A and Kanthasamy A G (2005) Protein kinase Cdelta is a key downstream mediator of manganese-induced apoptosis in dopaminergic neuronal cells. *J Pharmacol Exp Ther* 313:46-55.

Maguire-Zeiss K A, Short D W and Federoff H J (2005) Synuclein, dopamine and oxidative stress: co-conspirators in Parkinson's disease? *Brain Res Mol Brain Res* 134:18-23.

Merritt S E, Mata M, Nihalani D, Zhu C, Hu X and Holzman L B (1999) The mixed lineage kinase DLK utilizes MKK7 and not MKK4 as substrate. *J Biol Chem* 274:10195-10202.

Przedborski S (2005) Pathogenesis of nigral cell death in Parkinson's disease. *Parkinsonism Relat Disord* 11 Suppl 1:S3-7.

Reyland M E, Anderson S M, Matassa A A, Barzen K A and Quissell D O (1999) Protein kinase C delta is essential for etoposide-induced apoptosis in salivary gland acinar cells. *J Biol Chem* 274:19115-19123.

Silva R M, Kuan C Y, Rakic P and Burke R E (2005) Mixed lineage kinase-c-jun N-terminal kinase signaling pathway: a new therapeutic target in Parkinson's disease. *Mov Disord* 20:653-664.

Soltoff S P (2001) Rottlerin is a mitochondrial uncoupler that decreases cellular ATP levels and indirectly blocks protein kinase Cdelta tyrosine phosphorylation. *J Biol Chem* 276: 37986-37992.

Wang L H, Besirli C G and Johnson E M, Jr. (2004) Mixed-lineage kinases: a target for the prevention of neurodegeneration. *Annu Rev Pharmacol Toxicol* 44:451-474.

West A B, Dawson V L and Dawson T M (2005) To die or grow: Parkinson's disease and cancer. *Trends Neurosci* 28:348-352.

Yang Y, Kaul S, Zhang D, Anantharam V and Kanthasamy A G (2004) Suppression of caspase-3-dependent proteolytic activation of protein kinase C delta by small interfering RNA prevents MPP+-induced dopaminergic degeneration. *Mol Cell Neurosci* 25:406-421.

Yoshida K, Miki Y and Kufe D (2002) Activation of SAPK/JNK signaling by protein kinase Cdelta in response to DNA damage. *J Biol Chem* 277:48372-48378.

FIGURE LEGENDS

Figure 5:
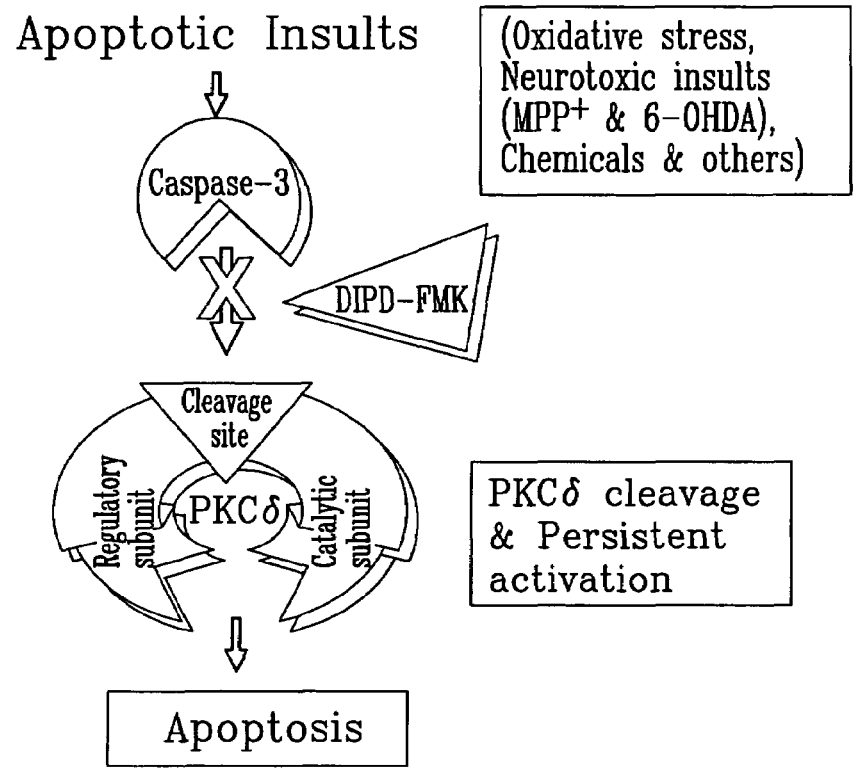
FIG. 5 is a diagram showing the proposed mechanism of action of the novel PKCδ cleavage inhibitor z-DIPD-fmk (SEQ ID NO:5): 1). Dopaminergic toxins MPP$^+$ and 6-OHDA activate caspase-3; 2) Activated caspase-3 mediate-sproteolytic cleavage of PKCδ; 3) Proteolytically active PKCδ mediates neuronal apoptosis; 4) DIPD (SEQ ID NO:5) peptide inhibitor directed against the PKCδ cleavage site. In essence, the cell permeable cleavage inhibitor z-DIPD-fmk (SEQ ID NO:5) should protect neuronal cells against apoptotic cell death.

FIG. 5. Proposed mechanism of action of the novel PKCδ cleavage inhibitor z-DIPD-fmk (SEQ ID NO:5): 1) Dopaminergic toxins MPP+ and 6-OHDA activate caspase-3; 2) Activated caspase-3 mediates proteolytic cleavage of PKCδ; 3) Proteolytically active PKCδ mediates neuronal apoptosis; 4) DIPD peptide inhibitor directed against the PKCδ cleavage site. In essence, the cell permeable cleavage inhibitor z-DIPD-fmk (SEQ ID NO:5) should protect neuronal cells against apoptotic cell death.

Figure 6A:
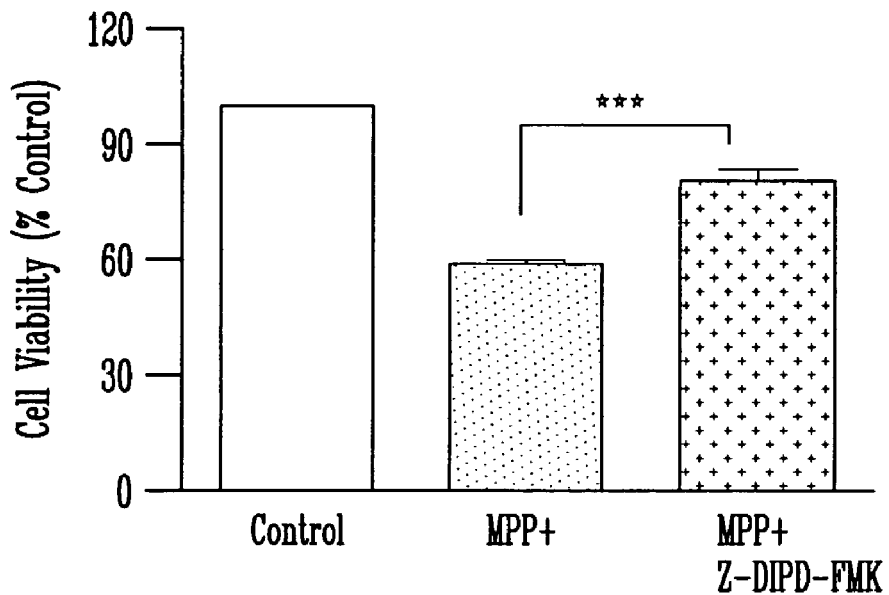
FIGS. 6A and 6B are graphs showing the effects of z-DIPD-fmk (SEQ ID NO:5) on MPP$^+$- and 6-OHDA-induced cytotoxicity in N27 mesencephalic neuronal cells. Each bar represents mean±SEM for n=6-9. Asterisks (*$p<0.05$ or **$p<0.01$) indicate significant difference compared with control cells, and pound sign (# $p<0.05$ or ## $p<0.01$) indicates significant differences between z-DIPD-fmk (SEQ ID NO:5)-co-treated and MPP$^+$ or 6-OHDA treated cells.
Figure 6B:
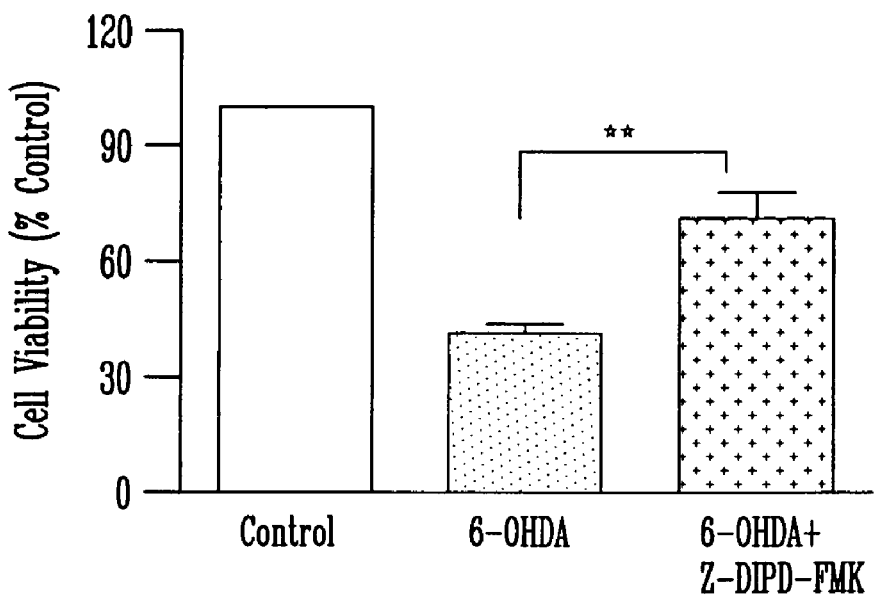

FIG. 6. Effect of z-DIPD-fmk (SEQ ID NO:5) on MPP+- and 6-OHDA-induced cytotoxicity in N27 mesencephalic neuronal cells. Briefly, N27 cells were treated with either 300 µM MPP+ for 36 hr or 100 µM 6-OHDA for 24 hr in the presence or absence of 50 µM z-DIPD-fmk (SEQ ID NO:5). Cytotoxicity was determined using the MTT assay as described in the methods section. Cell viability data in A., MPP+±z-DIPD-fmk (SEQ ID NO:5) treated cells and B, 6-OHDA±z-DIPD-fmk (SEQ ID NO:5) treated cells. Each bar represents mean±SEM for n=6-9. Asterisks (*p<0.05 or **p<0.01) indicate significant difference compared with control cells, and pound sign (# p<0.05 or ## p<0.01) indicates significant differences between z-DIPD-fmk (SEQ ID NO:5)-co-treated and MPP+ or 6-OHDA treated cells.

FIG. 7. Effect of z-DIPD-fmk (SEQ ID NO:5) on MPP+- and 6-OHDA-induced caspase-3 activation. Briefly, N27 cells were treated with either 300 µM MPP+ for 36 hr or 100 µM 6-OHDA for 24 hr in the presence or absence of 50 µM z-DIPD-fmk (SEQ ID NO:5). Cytosolic supernatants were collected and caspase activities were measured by incubating the supernatant with 50 µM Ac-DEVD-AFC (SEQ ID NO:6) (fluorogenic caspase-3 substrate) for 1 hr at 37° C., and expressed as fluorescent unit (FU) per mg protein per hr or as percent control. Caspase-3 activity in A., MPP+±z-DIPD-fmk (SEQ ID NO:5) treated cells and B, 6-OHDA±z-DIPD-fmk (SEQ ID NO:5) treated cells. Each bar represents mean±SEM for n=6-9. Asterisks (*p<0.05 or **p<0.01) indicate significant difference compared with control cells and pound sign (# p<0.05 or ## p<0.01) indicates significant differences between z-DIPD-fmk (SEQ ID NO:5)-co-treated and MPP+ or 6-OHDA treated cells.

Figure 8:
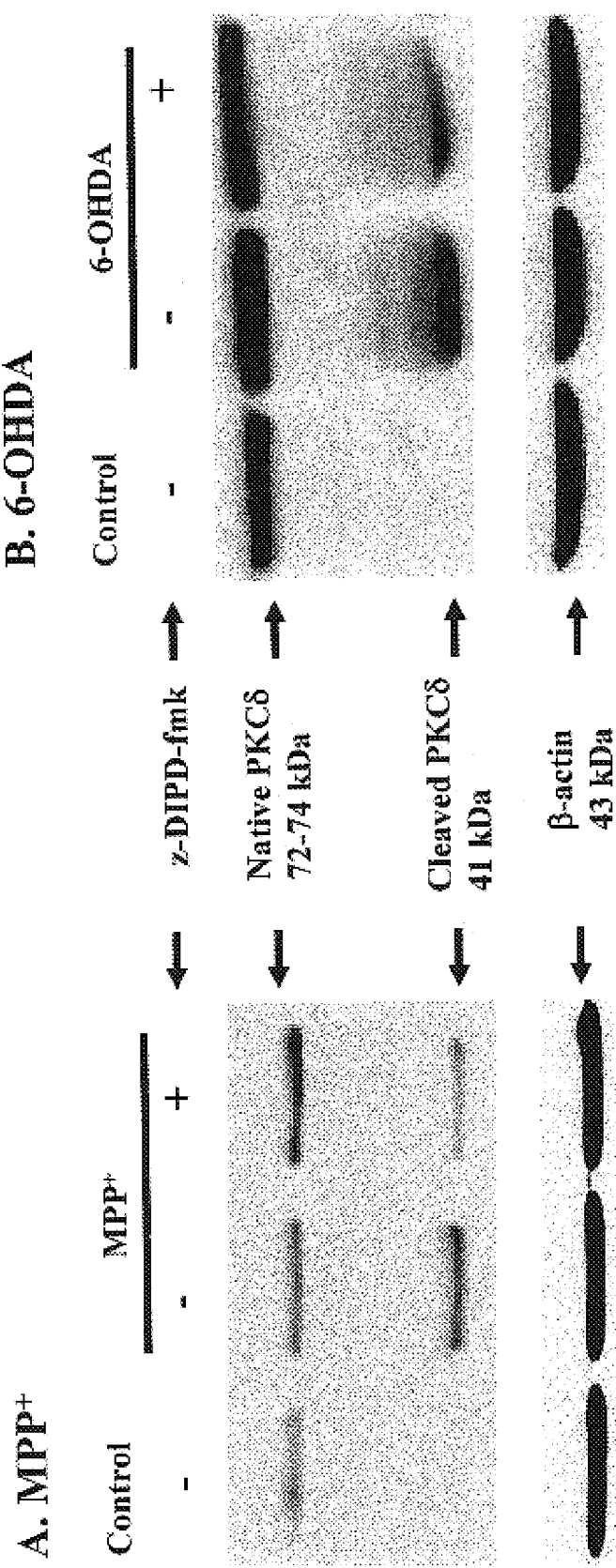
FIGS. 8A and 8B are Western blots showing the effect of z-DIPD-fmk (SEQ ID NO:5) on MPP$^+$- and 6-OHDA-induced PKCδ proteolytic cleavage. Western blot of A., MPP$^+$ ±z-DIPD-fmk (SEQ ID NO:5) treated cells and B, 6-OHDA±z-DIPD-fmk (SEQ ID NO:5) treated cells. Native PKCδ appears at 72-74 kDa and catalytically active cleaved PKCδ appears at around 41 kDa. Equal protein loading was confirmed by re-probing with â-actin.

FIG. 8. Effect of z-DIPD-fmk (SEQ ID NO:5) on MPP+- and 6-OHDA-induced PKCδ proteolytic cleavage. Briefly, N27 cells were treated with either 300 µM MPP+ for 36 hr or 100 µM 6-OHDA for 24 hr in the presence or absence of 50 µM z-DIPD-fmk (SEQ ID NO:5). After treatment, cytosolic fractions were collected, and equal amounts of proteins were resolved on 10% SDS-PA GE followed by polyclonal PKCδ antibody as described in the methods section. Western blot of A., MPP+±z-DIPD-fmk (SEQ ID NO:5) treated cells and B, 6-OHDA±z-DIPD-fmk (SEQ ID NO:5) treated cells. Native PKCδ appears at 72-74 kDa and catalytically active cleaved PKCδ appears at around 41 kDa. Equal protein loading was confirmed by re-probing with â-actin.

Figure 9B:
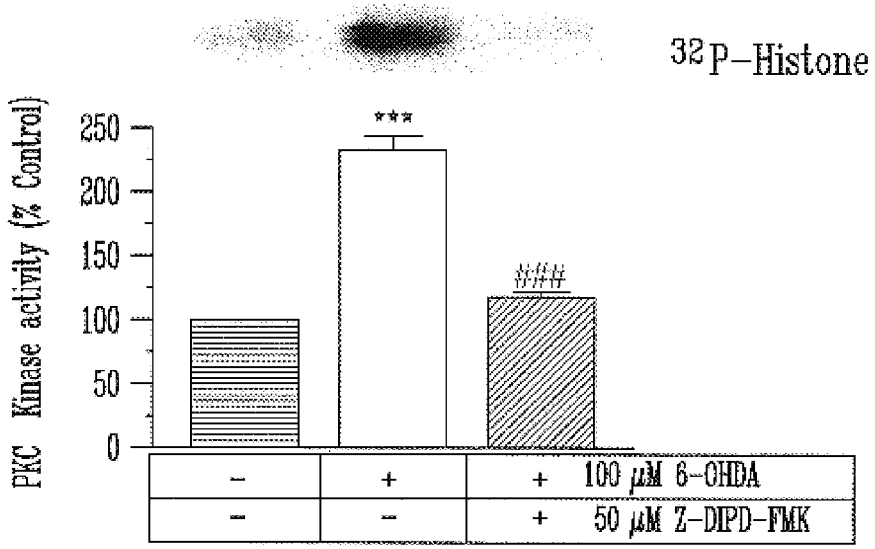

FIG. 9. Effect of z-DIPD-fmk (SEQ ID NO:5) on MPP+- and 6-OHDA-induced PKCδ kinase activity. Briefly, N27 cells were treated with either 300 µM MPP+ for 36 hr or 100 µM 6-OHDA for 24 hr in the presence or absence of 50 µM z-DIPD-fmk (SEQ ID NO:5. After treatment cell lysates were collected and subjected to immunoprecipitation kinase assays as described in the methods section. PKCδ kinase activity in Western blot of A., MPP+±z-DIPD-fmk (SEQ ID NO:5) treated cells and B, 6-OHDA±z-DIPD-fmk (SEQ ID NO:5) treated cells. Phosphorylated histone bands were quantified by a PhosphoImager after scanning the dried gel and were expressed as percent of control. The values represent mean±SEM from two separate experiments performed in duplicate. Asterisks (*p<0.05 or **p<0.01) indicate significant difference compared with control cells and pound sign (# p<0.05 or ## p<0.01) indicates significant differences between z-DIPD-fmk (SEQ ID NO:5)-co-treated and MPP+ or 6-OHDA treated cells.

Figure 10B:
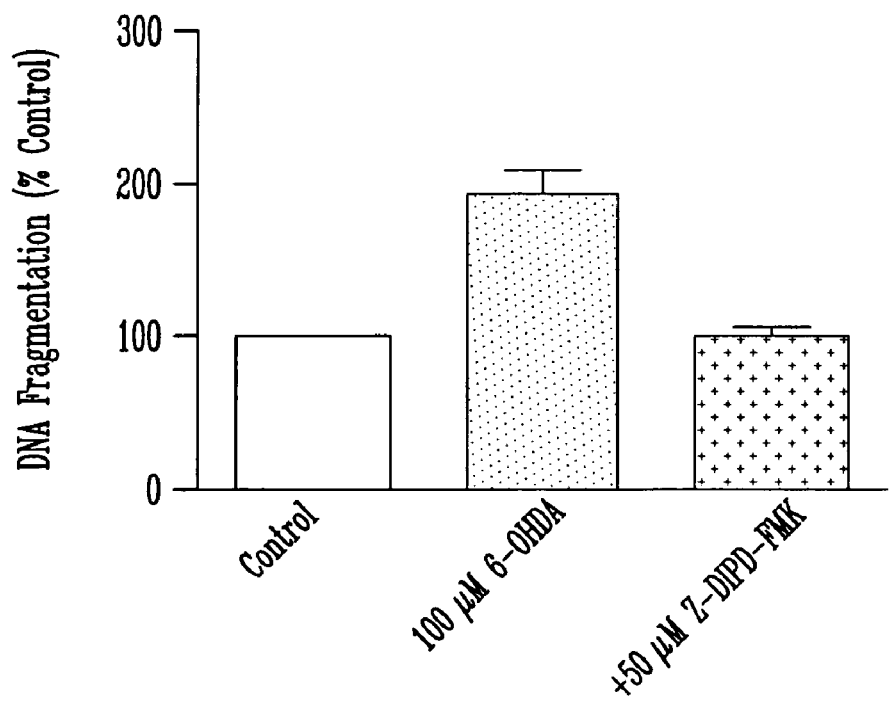

FIG. 10. Effect of z-DIPD-fmk (SEQ ID NO:5) on MPP+- and 6-OHDA-induced apoptotic cell death. Briefly, N27 cells were treated with either 300 µM MPP+ for 36 hr or 100 µM 6-OHDA for 24 hr in the presence or absence of 50 µM z-DIPD-fmk (SEQ ID NO:5). Apoptotic cell death was determined by measuring DNA fragmentation in an ELISA sandwich assay as described in the methods section. DNA fragmentation in A., MPP+±z-DIPD-fmk (SEQ ID NO:5) treated cells and B, 6-OHDA±z-DIPD-fmk (SEQ ID NO:5) treated cells. Each bar represents mean±SEM for n=6-9. Asterisks (*p<0.05 or **p<0.01) indicate significant difference compared with control cells and pound sign (# p<0.05 or ## p<0.01) indicates significant differences between z-DIPD-fmk (SEQ ID NO:5)-co-treated and MPP+ or 6-OHDA treated cells.

Figure 11:
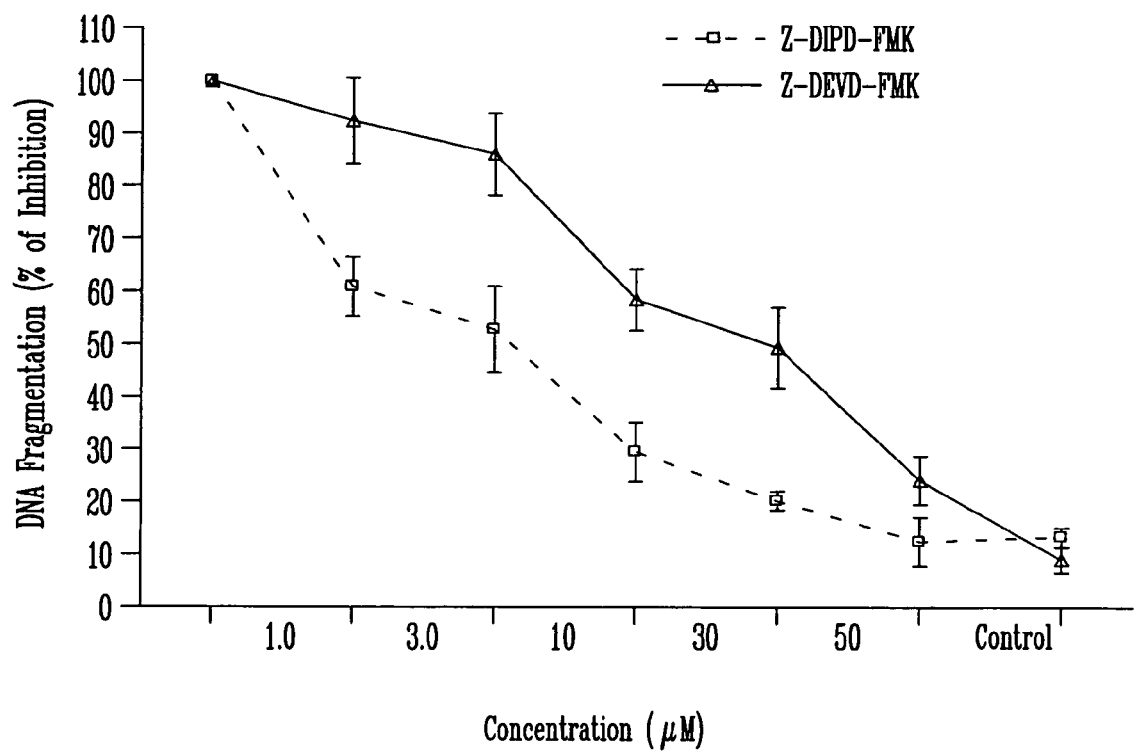
FIG. 11 is a graph showing the comparative effect of z-DIPD-fmk (SEQ ID NO:5) and z-DEVD-fmk (SEQ ID NO:6) on 6-OHDA-induced DNA fragmentation. IC$_{50}$ values of z-DIPD-fmk (SEQ ID NO:5) and z-DIPD-fmk (SEQ ID NO:5) were significantly different (p<0.02, Welch-corrected unpaired t-test).

FIG. 11. Comparative effect of z-DIPD-fmk (SEQ ID NO:5) and z-DEVD-fmk (SEQ ID NO:6) on 6-OHDA-induced DNA fragmentation. Briefly, N27 cells were treated with 100 μM 6-OHDA for 24 hr in the presence or absence of 1-50 μM z-DIPD-fmk (SEQ ID NO:5) or 1-50 μM z-DEVD-fmk (SEQ ID NO:6). The data are expressed as percent inhibition compared to 6-OHDA treatment and analyzed by three-parameter logistic regression ($IC_{50}$ and 95% confidence interval). $IC_{50}$ values of z-DIPD-fmk (SEQ ID NO:5) and z-DIPD-fmk (SEQ ID NO:5) were significantly different ($p<0.02$, Welch-corrected unpaired t-test).

FIG. 12. z-DIPD-fmk (SEQ ID NO:5) protects against $MPP^+$- and 6-OHDA-induced TH neuronal cell and neurite loss. Primary mesencephalic cultures were isolated from E18 pups (C57 black mice) and cultured as described in the methods section. Briefly, primary neurons were cultured and grown on laminin coated cover slips. The cultures were then exposed to 10 μM $MPP^+$ or 30 μM 6-OHDA for 24 hr in the presence or absence of 10-50 μM z-DIPD-fmk (SEQ ID NO:5). After treatment primary neurons were fixed and immunostained for TH. Primary staining was followed by secondary staining with Cy3-conjugated antibody, mounted, and viewed under a Nikon TE2000 fluorescence microscope as described in the methods section. Representative images immunostained for TH are shown in A, $MPP^+$ and C, 6-OHDA. TH cell count and neuronal process length were quantified using Metamorph image analysis software as described in the methods section. Quantitative data of TH cell count and neuronal process length in image sets A and B are shown in B, $MPP^+$ and D, 6-OHDA respectively.

FIG. 13. Design of triple tandem human PKCδ cleavage site motif DMQD (SEQ ID NO:7) and cleavage site resistant motif DMQA (SEQ ID NO:8). The oligonucleotide and amino acid sequence for the human PKCδ cleavage site motif DMQD (SEQ ID NO:7) and human PKCδ cleavage resistant motif DMQA (SEQ ID NO:8). Refer to the methods section for details.

Figure 14A:
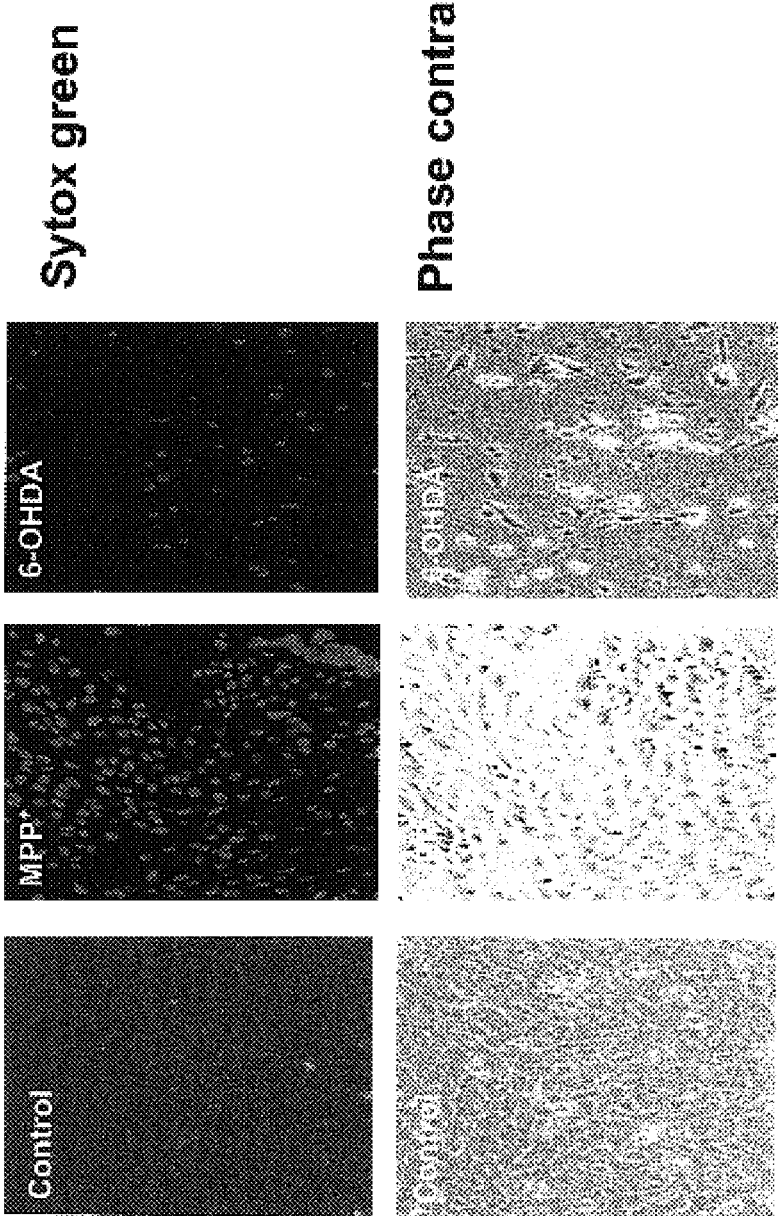

FIG. 14. Expression of DMQD (SEQ ID NO:7) and DMQA (SEQ ID NO:8) protects against $MPP^+$- and 6-OHDA-induced cytotoxicity in N27 mesencephalic neuronal cells. N27 cells were transfected with lentiviral vectors and then treated with either 300 μM $MPP^+$ for 36 hr or 100 μM 6-OHDA for 24 hr. Cytotoxicity was determined using Sytox imaging. A) Control N27 cells treated with $MPP^+$ and 6-OHDA. B) DMQD (SEQ ID NO:7)-transfected cells treated with $MPP^+$ and 6-OHDA, and C) DMQA (SEQ ID NO:8) transfected cells treated with $MPP^+$ and 6-OHDA. Increase in number of Sytox green fluorescence cells represents increase in neurotoxicity. DMQD (SEQ ID NO:7) and DMQA (SEQ ID NO:8) transfected cells protected against $MPP^+$ and 6-OHDA neurotoxicity as demonstrated by the lower number of Sytox green fluorescence positive cells as compared to control cells.

What is claimed is:

1. A method of treating Parkinson's disease, Huntington disease, ischemia, stroke, a cardiovascular disease or an inflammatory disease comprising: administering an effective amount of the peptide Asp-Ile-Pro-Asp (SEQ ID NO: 5), optionally modified at the N- and/or C-terminus with N-benzyloxycarbonyl or fluoromethyl ketone, to an animal in need thereof, wherein the effective amount is sufficient to inhibit PKCδ cleavage.

2. The method of claim 1 wherein the peptide inhibitor inhibits caspase 3.

3. The method of claim 2 wherein said peptide inhibitor binds irreversibly to the PKCδ cleavage site.

4. A polypeptide consisting of Asp-Ile-Pro-Asp (SEQ ID NO: 5) with optional modifications to C- and N-terminus; wherein the said polypeptide inhibits PKCδ cleavage by caspase-3.

5. The polypeptide of claim 4 wherein the polypeptide further comprises the chemical addition of N-benzyloxycarbonyl at the N-terminal.

6. The polypeptide of claim 4 wherein the inhibitor further comprises a tail at the C-terminus of the polypeptide for facilitating cell membrane permeability.

7. The polypeptide of claim 4 wherein said inhibitor is chemically modified to protect the inhibitor from protease degradation.

8. The polypeptide of claim 4 further comprising a pharmaceutical carrier.

9. The method of claim 1 wherein the peptide is modified at the N-terminus by addition of N-benzyloxycarbonyl.

10. The method of claim 1 wherein the peptide is modified at the C-terminus by addition of a fluoromethyl ketone.

11. A method of treating Parkinson's disease, Huntington disease, ischemia, stroke, a cardiovascular disease or an inflammatory disease comprising: administering an effective amount of the peptide Asp(Ome)-Ile-Pro-Asp(Ome)-fluoromethyl ketone (FMK), to an animal in need thereof, wherein the effective amount is sufficient to inhibit PKCδ cleavage.

* * * * *

UNITED STATES PATENT AND TRADEMARK OFFICE
CERTIFICATE OF CORRECTION

PATENT NO. : 7,632,819 B1  Page 1 of 1
APPLICATION NO. : 11/262677
DATED : December 15, 2009
INVENTOR(S) : Anumantha G. Kanthasamy It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 724 days.

Signed and Sealed this

Twenty-first Day of December, 2010

David J. Kappos
*Director of the United States Patent and Trademark Office*